US007442546B2

(12) United States Patent
Humes

(10) Patent No.: US 7,442,546 B2
(45) Date of Patent: *Oct. 28, 2008

(54) METHOD OF MODULATING INFLAMMATORY RESPONSE

(75) Inventor: H. David Humes, Ann Arbor, MI (US)

(73) Assignee: The Regents of the University of Michigan, Ann Harbor, MI (US)

(*) Notice: Subject to any disclaimer, the term of this patent is extended or adjusted under 35 U.S.C. 154(b) by 429 days.

This patent is subject to a terminal disclaimer.

(21) Appl. No.: 10/372,303

(22) Filed: Feb. 25, 2003

(65) Prior Publication Data
US 2003/0223969 A1 Dec. 4, 2003

Related U.S. Application Data

(60) Provisional application No. 60/364,128, filed on Mar. 15, 2002.

(51) Int. Cl.
C12N 5/00 (2006.01)

(52) U.S. Cl. ............... 435/369; 424/93.7; 435/325; 435/395; 435/400; 604/4.01; 604/5.02; 604/6.01; 604/6.04; 623/23.65

(58) Field of Classification Search ......... 435/369, 435/325, 395, 400; 604/4.01, 5.02, 6.04, 604/6.01; 623/23.65; 424/93.7
See application file for complete search history.

(56) References Cited

U.S. PATENT DOCUMENTS

| 3,734,851 | A | 5/1973 | Matsumura |
| 4,242,460 | A | 12/1980 | Chick et al. |
| 4,354,933 | A | 10/1982 | Lester |
| 4,973,493 | A | 11/1990 | Guire |
| 5,002,582 | A | 3/1991 | Guire et al. |
| 5,360,790 | A | 11/1994 | Humes |
| 5,414,075 | A | 5/1995 | Swan et al. |
| 5,429,938 | A | 7/1995 | Humes |
| 5,437,994 | A | 8/1995 | Emerson et al. |
| 5,459,069 | A | 10/1995 | Palsson et al. |
| 5,499,976 | A | 3/1996 | Dalton |
| 5,516,680 | A | 5/1996 | Naughton et al. |
| 5,549,674 | A | 8/1996 | Humes et al. |
| 5,550,050 | A | 8/1996 | Holland et al. |
| 5,580,697 | A | 12/1996 | Keana et al. |
| 5,605,822 | A | 2/1997 | Emerson et al. |
| 5,639,275 | A | 6/1997 | Baetge et al. |
| 5,653,975 | A | 8/1997 | Baetge et al. |
| 5,656,481 | A | 8/1997 | Baetge et al. |
| 5,661,133 | A | 8/1997 | Leiden et al. |
| 5,676,943 | A | 10/1997 | Baetge et al. |
| 5,686,289 | A | 11/1997 | Humes et al. |
| 5,733,727 | A | 3/1998 | Field |
| 5,763,266 | A | 6/1998 | Palsson et al. |
| 5,773,286 | A | 6/1998 | Dionne et al. |
| 5,795,790 | A | 8/1998 | Schinstine et al. |
| 5,833,978 | A | 11/1998 | Tremblay |
| 5,843,781 | A | 12/1998 | Ballerman et al. |
| 5,858,653 | A | 1/1999 | Duran et al. |
| 5,906,817 | A | 5/1999 | Moullier et al. |
| 5,919,449 | A | 7/1999 | Dinsmore |
| 5,965,125 | A | 10/1999 | Mineau-Hanschke |
| 6,060,270 | A | 5/2000 | Humes |
| 6,110,209 | A | 8/2000 | Stone |
| 6,150,164 | A | 11/2000 | Humes |
| 6,156,304 | A | 12/2000 | Glorioso et al. |
| 6,653,131 | B2 * | 11/2003 | Humes ................ 435/369 |

FOREIGN PATENT DOCUMENTS

| GB | 1 479 002 | 6/1974 |
| WO | WO 89/01967 | 3/1989 |
| WO | WO 91/00119 | 1/1991 |
| WO | WO 92/07615 | 5/1992 |
| WO | WO 93/17696 | 9/1996 |

OTHER PUBLICATIONS

H. Humes, et al., "Replacement of Renal Function in Uremic Animals with a Tissue-Engineered Kidney", Nature Biotechnology, vol. 17, pp. 451-455, 1999.
R. Bone, "Systemic Inflammatory Response Syndrome: A Unifying Concept of Systemic Inflammation", Sepsis and Multiorgan Failure, 1997, pp. 3-10.
H. Humes, et al., "Tissue Engineering of a Bioartificial Renal Tubule Assist Device: In Vitro Transport and Metabolic Characteristics", Kidney International, vol. 55, 1999, pp. 2502-2514.
H. Humes, "Bioartificial Kidney for Full Renal Replacement Therapy", Seminars in Nephrology, vol. 20, No. 1, Jan. 2000, pp. 71-82.
J. Walker, et al., "The Language of Biotechnolgy", 1988, p. 126.
R. Freshney, "Culture of Animal Cells", A Manual of Basic Technique, 2nd Ed., 1987, pp. 1-13 and 197-206.
S. MacKay et al., "Tissue Engineering of a Bioartificial Renal Tubule", ASAIO Journal, vol. 44, No. 3, May-Jun. 1998, pp. 179-183.
S. Pobojewski, "U Researchers Unveil Component of Bio-Artificial Kidney", The University Record, May 24, 1999.
C. Natanson, et al., "Role of Endotoxemia in Cardiovascular Dysfunction and Mortality", The Journal of Clinical Investigation, Inc., vol. 83, Jan. 1989, pp. 243-251.
B. Freeman, et al., "Continuous Arteriovenous Hemofiltration Does Not Improve Survival in a Canine Model of Septic Shock", Journal of the American College of Surgeons, Mar. 1995, vol. 180, pp. 286-291.
J. Kellum, "Immunomodulation In Sepsis: The Role of Hemofiltration", Minerva Anestesiologica, vol. 65, No. 6, pp. 410-418.
G. Bernard, M.D., et al., "Efficacy and Safety of Recombinant Human Activated Protein C for Severe Sepsis", The New England Journal of Medicine, vol. 344, No. 10, Mar. 8, 2001, pp. 699-709.
D. Tran et al., "Age, Chronic Disease, Sepsis, Organ System Failure, and Mortality in a Medical Intensive Care Unit", Critical Care Medicine, vol. 18, No. 5, pp. 474-479, May 1990.
S. Donnelly et al., "Mediators, Mechanisms and Mortality in Major Trauma", Resuscitation, vol. 28, pp. 87-92, 1994.

(Continued)

Primary Examiner—L B Lankford
Assistant Examiner—Taeyoon Kim
(74) Attorney, Agent, or Firm—Hamilton, Brook, Smith & Reynolds, P.C.

(57) ABSTRACT

A method of immunomodulation by contacting the bodily fluid of a patient with renal tubule cells outside of the kidney.

7 Claims, 22 Drawing Sheets

OTHER PUBLICATIONS

R. Bone, M.D., et al., "A Controlled Clinical Trial of High-Dose Methylprednisolone in the Treatment of Severe Sepsis and Septic Shock", The New England Journal of Medicine, vol. 317, No. 11, pp. 653-658.

K. Horn, "Evolving Strategies in the Treatment of Sepsis and Systemic Inflammatory Response Syndrome (SIRS)", Q.J. Med, 1998, vol. 91, pp. 265-277.

M. Pinsky, "Serum Cytokine Levels in Human Septic Shock", Chest, vol. 103, No. 2, Feb. 1993, pp. 565-575.

C. Marty, et al., "Circulating Interleukin-8 Concentration in Patients with Multiple Organ Failure of Septic and Nonseptic Origin", Critical Care Medicine, vol. 22, No. 4, pp. 673-679, Apr. 1994.

P. Damas, M.D., Ph.D., et al., "Tumor Necrosis Factor and Interleukin-1 Serum levels During Severe Sepsis in Humans", Critical Care Medicine, vol. 17, No. 10, pp. 975-978, Oct. 1989.

C. Dinarello, "The Proinflammatory Cytokines Interleukin-1 and Tumor Necrosis Factor and Treatment of the Septic Shock Syndrome", The Journal of Infectious Diseases, 1991: 163, pp. 1177-1184.

T. Calandra, et al., "Prognostic Values of Tumor Necrosis Factor/Cachectin, interleukin-1, Interferon-$\alpha$, and Interferon-y in the Serum of Patients with Septic Shock", The Journal of Infectious Diseases, 1990: 161, pp. 982-987.

J. Jiang, et al., "Plasma Cytokines and Endotoxin Levels in Patients with Severe Injury and Their Relationship with Organ Damage", Injury, vol. 28, No. 8, pp. 509-513, 1997.

D. Breen, et al., "Acute Renal Failure as a Part of Multiple Organ Failure: The Slippery Slope of Critical Illness", Kidney International, vol. 53, Suppl. 66, 1998, pp. S25-S33.

M. Sarnak, et al., "Mortality Caused by Sepsis in Patients with End-Stage Renal Disease Compared with the General Population", Kidney International, vol. 58, 2000, pp. 1758-1764.

M. Girndt, et al., "Production in Interleukin-6, Tumor Necrosis Factor $\alpha$ and Interleukin-10 in vitro Correlates with the Clinical Immune Defect in Chronic Hemodialysis Patients", Kidney International, vol. 47, 1995, pp. 559-565.

M. Girndt, et al., "Impaired Cellular Immune Function in Patients with End-Stage Renal Failure", Nephrol Dial Transplant, 1999: 14, pp. 2807-2810.

M. Thomas, M.D., Ph.D., et al., "Hyptovitaminosis D in Medical Inpatients", The New England Journal of Medicine, vol. 338, No. 12, Mar. 19, 1998, pp. 777-783.

A. Trifillis, et al., "Isolation, Culture and Characterization of Human Renal Tubular Cells", The Journal of Urology, vol. 133, February, pp. 324-329.

C. Detrisac, et al., "Tissue Culture of Human Kidney Epithelial Cells of Proximal Tubule Orgin", Kidney International, vol. 25, 1984, pp. 383-390.

R. Bone, M.D., "Why Sepsis Trials Fail", JAMA, Aug. 21, 1996, vol. 276, No. 7, pp. 565-566.

R. Bone, M.D., "Toward a Theory Regarding the Pathogenesis of the Systemic Inflammatory Response Syndrom: What We Do and Do Not Know About Cytokine Regulation", Crit Care Med., 1996, vol. 24, No. 1, pp. 163-172.

C. Hack, et al., "Interleukin-8 in Sepsis: Relation to Shock and Inflammatory Mediators", Infection and Immunity, Jul. 1992, vol. 60, No. 7, pp. 2835-2842.

R. Bone, M.D., "Immunologic Dissonance: A Continuing Evolution in Our Understanding of the Systemic Inflammatory Response Syndrome(SIRS) and the Multiple Organ Dysfunction Syndrome (MODS)", Ann Tern Med., 1996, vol. 125, pp. 680-687.

R. Bone, M.D., "Sepsis: A New Hypothesis for Pathogenesis of the Disease Process", Chest, vol. 112, No. 1, Jul. 1997, pp. 235-243.

J. Reeves, et al., "Continuous Plasmafiltration in Sepsis Syndrome", Crit Care Med., vol. 27, No. 10, pp. 2096-2104.

A. De Vriese, et al., "Continuous Renal Replacement Therapies in Sepsis: Where are the Data?", Nephrol Dial Transplant, 1998, vol. 13, pp. 1362-1364.

J. Vincent, M.D., et al., "Phase II Multicenter Clinical Study of the Platelet-Activating Factor Receptor Antagonist BB-882 in the Treatment of Sepsis", Crit Care Med., vol. 28, No. 3, 2000, pp. 638-642.

Z. Quezado, et al., "New Strategies for Combatting Sepsis: The Magic Bullets Missed the Mark . . . But the Search Continues", Tibtech, Feb. 1995, vol. 13, pp. 56-63.

J. Christman, M.D., "Strategies for Blocking the Systemic Effects of Cytokines in the Sepsis Syndrome", Critical Care Medicine, vol. 23, No. 5, pp. 955-963, 1995.

M. Kielar, et al., The Liver Regulates Renal Ischemic Injury: A Possible Role for Renal IL6 and Hepatic IL 10?, Abstract.

K. Lally, et al., "The Role of Anti-Tumor Necrosis Factor-$\alpha$ and Interleukin-10 in Protecting Murine Neonates from Escherichia coli, Sepsis", Journal of Pediatric Surgery, vol. 35, No. 6, Jun. 2000, pp. 852-855.

K. Walley, et al., "Balance of Inflammatory Cytokines Related to Severity and Mortality of Murine Sepsis", Infection and Immunity, vol. 64, No. 11, pp. 4733-4738, 1996.

T. Matsumoto, et al., "Effect of Interleukin-10 on Gut-Derived Sepsis Caused by Pseudomonas Aeruginosa in Mice", Antimicrobial Agents and Chemotherapy, Nov. 1998, vol. 42, No. 11, pp. 2853-2857.

A. Merchant, et al., "Interleukin-10 Controsl Interferon-y and Tumor Necrosis Factor Production During Experimental Endotoxemia", Eur. J. Immunol., 1994, vol. 24, pp. 1167-1171.

Z. Massy, "Reversal of Hyperhomocyst(e) Inaemia in Chronic Renal Failure-Is Folic or Folinic Acid the Answere?", Nephrol Dial Transplant, 1999, vol. 14, pp. 2813-2815.

R. Vanholder, et al., "p-Cresol: A Toxin Revealing Many Neglected But Relevant Aspects of Uraemic Toxicity", Nephol Dial Transplatn, 1999, vol. 14, pp. 2810-2812.

J. Bommer, "Saving erythropoietin by Administering L-Carnitine?", Nephrol Dial Transplant, 1999, vol. 14, pp. 2819-2821.

M. Dratwa, "Pre-Emptive CAPD-What Are the Arguments?", Nephrol Dial Transplant, 1999, vol. 14, pp. 2822-2823.

B. Maes, et al., "Anti- Interleukin-2 Receptor Monoclonal Antibodies in Renal Transplant", Nephrol Dial Transplant, 1999, vol. 14, pp. 2824-2826.

A. Mogyorosi, et al., "GLUT1 and TGF-$\beta$: The Link Between Hyperglycaemia and Diabetic Nephropathy", Nephrol Dial Transplant, 1999, vol. 14, pp. 2827-2829.

R. Montesano, et al., "Induction of Eipthelial Tubular Morphogenesis in Vitro by Fibroblast-Derived Soluble Factors", Cell, vol. 66, Aug. 23, 1991, pp. 697-711.

H. Humes, et al., "Effects of Transforming Growth Factor-$\beta$, Transforming Growth Factor-$\alpha$, and Other Growth Factors on Renal Proximal Tubule Cells", Laboratory Investigation, vol. 64, No. 4, pp. 538-545, 1991.

F. Watt, et al., "Out of Eden: Stem Cells and Their Niches", Science, vol. 287, Feb. 25, 2000, pp. 1427-1430.

Q. Al-Awqati, "Cellular and Molecular Mechanisms of Renal Development and Tubulogenesis", Current Science, pp. 53-58.

S. Orkin, M.D., "Report and Recommendations of the Panel to Assess the Nih Investment in Research on Gene Therapy".

T. Ip, et al., "Renal Epithelial-Cell-Controlled Solute Transport Across Permeable Membranes as the Foundation for a Bioartificial Kidney", Artificial Organs, vol. 13, No. 1, pp. 58-65, 1989.

E. Chaikof, "Engineering and Materil Considerations in Islet Cell Transplantation", Annu. Rev. Biomed. Eng., 01: pp. 103-127, 1999.

A. Jensen, et al., Expression of Sonic hedgehog and Its Putative Role as a Precursor Cell Mitogen in the Developing Mouse Retina.

M. Horney, et al., "Elevated Glucose Increases Mesangial Cell Sensitivity to Insulin-Like Growth Factor I", The American Physiological Society, pp. F1045-F1053, 1998.

B. Brenner, M.D.., "Mechanics of Glomerular Ultrafiltration", The New England Journal of Medicine, vol. 297, 1997, pp. 148-154.

J. Zwiebel, et al., "High-Level Recombinant Gene Expression in Rabbit Endothelial Cells Transduced by Retroviral Vectors", Science, vol. 243, pp. 220-222.

D. Dichek, M.D., et al., "Seeding of Intravascular Stents with Genetically Engineered Endothelial Cells", Circulation, vol. 80, No. 5, Nov. 1989, pp. 1347-1353.

B. Brenner, M.D., et al., "Molecular Basis of Proteinuria of Glomerular Origin", The New England Journal of Medicine, Apr. 13, 1978, vol. 298, No. 15, pp. 826-833.

L. Shea, et al., "DNA Delivery From Polymer Matrices for Tissue Engineering", Nature Biotechnology, vol. 17, Jun. 1999, pp. 551-554.

M. Hu, et al., "FGF-18, a Novel Member of the Fibroblast Growth Factor Family, Stimulates Hepatic and Intestinal Proliferation", Molecular and Cellular Biology, Oct. 1998, pp. 6063-6074, vol. 18, No. 10.

J. Folkman, et al., "Angiogenesis", The Journal of Biological Chemistry, vol. 267, No. 16, Jun. 1992, pp. 10931-10934.

J. Madri, et al., "Phenotypic Modulation of Endothelial Cells by Transforming Growth Factor-β Depends Upon the Composition and Organization of the Extracellular Matrix", The Journal of Cell Biology, vol. 106, Apr. 1988, pp. 1375-1384.

Y. Tsurumi, M.D., et al., "Direct Intramuscular Gene Transfer of Naked DNA Encoding Vascular Endothelial Growth Factor Augments Collateral Development and Tissue Perfusion", Circulation, vol. 94, No. 12, Dec. 15, 1996, pp. 3281-3290.

S. Patel, et al., "Safety of direct Myocardial Administration of an Adenovirus Vector Encoding Vascular Endothelial Growth Factor 121", Human Gene Therapy, vol. 10, pp. 1331-1348, May 20, 1999.

Written Opinion, International Preliminary Examining Authority, Sep. 30, 2004.

J. Wilson, et al., "Implantation of Vascular Grafts Lined with Genetically Modified Endothelial Cells", Science, vol. 224, pp. 1344-1346, Jun. 16, 1989.

G. Brady, et al., "Solid Freeform Fabrication of Ceramics via Stereolithography", Department of Materials Science, University of Michigan, 1998, pp. 39-43.

B. Busse, et al., "Bioreactors for Hybrid Liver Support: Historical Aspects and Novel Designs", Busse & Gerlach: Bioreactors for Hybrid Liver Support, Annals New York Academy of Sciences, pp. 326-339.

N. Trivedi, et al., "Improved Vascularization of Planner Membrane Diffusion Devices Following Continuous Infusion of Vascular Endothelial Growth Factor", Cell Transplantation, vol. 9, pp. 115-124, 2000.

D. Bourell, et al., "Solid Freeform Fabrication Symposium", Aug. 12-14, 1996, The University of Texas at Austin.

D. Dimos, et al., "Solid Freeform and Additive Fabrication", Materials Research Society of Symposium Proceedings, vol. 542, Nov. 30-Dec. 1, 1998.

P. Jacobs, Ph.D., "Stereolithography and Other RP&M Technologies for Rapid Prototyping to Rapid Tooling", Society of Manufacturing Engineers, ASME Press, New York, NY, 1996, pp. 1-392.

Voldman, et al., "Microfabrication in Biology and Medicine", Annu. Rev. Biomed. Eng.:1(1), pp. 401-425.

B.R. Olsen, "Matrix Molecules and Their Ligands", Principles of Tissue Engineering, pp. 48-65, 1997.

R. Calafiore, et al., "Coherent Microcapsules for Pancreatic Islet Transplantation: A New Approach for Bioartifical Pancreas", Transplantation Proceedings, vol. 28, No. 2, Apr. 1996: pp. 812-813.

H. Hayashi, et al., "Long Survival of Xenografted Bioartificial Pancreas with a Mesh-Reinforced Polyvinyl Alcohol Hydrogel Bag Employing a B-Cell Line (MIN6)", Transplantation Proceedings, vol. 28, No. 3 Jun. 1996: pp. 1428-1429.

K. Naruse, et al., "Efficacy of a Bioreactor Filled with Porcine Hepatocytes Immobilized on Nonwoven Fabric for Ex Vivo Direct Hemoperfusion Treatment of Liver Failure in Pigs", International Society for Artificial Organs, 22(12): pp. 1031-1037, Blackwell Science, Inc., 1998.

C. Delaunay, et al., "Glucose-Insulin Kinetics of a Bioartificial Pancreas Made of an AN69 Hydrogel Hollow Fiber Containing Porcine Islets and Implanted in Diabetic Mice", International Society for Artificial Organs, 22(4): pp. 291-299, Blackwell Science, Inc., 1998.

V. Dixit, et al., The Bioartificial Liver: State-of-the-Art, Eur. J. Surg., 1998: Suppl. 582: pp. 71-76.

H. Ohgawara, et al., "Membrane Immunoisolation of a Diffusion Chamber for a Bioartificial Pancreas", International Society for Artificial Organs, 22(9), 1998, pp. 788-794.

S. K. Hunter, et al., "Encapsulated β-islet cells as a bioartificial pancreas to treat insulin-dependent diabetes during pregnancy", Am. J. Obstet. Gynecol, vol. 177, No. 4, pp. 746-752.

M. R. Pillarella, "Theoretical Analysis of the Effect of Convective Flow on Solute Transport and Insulin Release in a Hollow Fiber Bioartificial Pancreas", Journal of Biomechanical Engineering, May 1990, vol. 112, pp. 220-228.

J. A. Thompson, et al., "Site-Directed Neovessel Formation in Vivo", Science Reports, Sep. 9, 1988, pp. 1349-1352.

S. E. Feinberg, et al., "Role of Biomimetics in Reconstruction of the Temporomandibular Joint", Oral and Maxillofacial Surgery Clinics of North America, vol. 12, No. 1, Feb. 2000, pp. 149-160.

N. E. Mukundan, et al., "Oxygen Consumption Rates of Free and Alginate-entrapped βTC3 Mouse Insulinoma Cells", Biochemical and Biophysical Research Communications, vol. 210, No. 1, May 5, 1995, pp. 113-118.

Y. Tanaka, et al., "Generation of an autologous tissue (matrix) flap by combining and arteriovenous shunt loop with artificial skin in rats: preliminary report", British Journal of Plastic Surgery, (2000), 53, pp. 51-57.

R. Mian, et al., "Formation of New Tissue from an Arteriovenous Loop in the Absence of Added Extracellular Matrix", Tissue Engineering, vol. 6, No. 6, 2000, pp. 595-603.

G. Ahrendt, et al., "Angiogenic Growth Factors: A Review for Tissue Engineering", Tissue Engineering, vol. 4, No. 2, 1998, pp. 117-131.

C. K. Colton, "Engineering challenges in cell-encapsulation technology", Tibtech, May 1996, vol. 14, pp. 158-162.

C. K. Colton, "Bioengineering in Development of the Hybrid Artificial Pancreas", Journal of Biomechanical Engineering, vol. 113, May 1991, pp. 152-170.

R. P. Lanza, et al., "Transplantation of Islet Allografts Using a Diffusion-Based Biohybrid Artificial Pancreas: Long-Term Studies in Diabetic, Pancreatectomized Dogs", Transplantation Proceedings, vol. 25, No. 1, Feb. 1993: pp. 978-980.

C. A. Ramirez, et al., "In Vitro Perfusion of Hybride Artificial Pancreas Devices at Low Flow Rates", ASAIO Journal 1992, pp. M443-M449.

S. Esser, et al., "Vascular Endothelial Growth Factor Induces Endothelial Fenestrations In Vitro", The Journal of Cell Biology, vol. 140, No. 4, Feb. 23, 1998, pp. 947-959.

Y.S. Chang, et al., "Effect of Bascular Endothelial Growth Factor on Cultured Endothelial Cell Monolayer Transport Properties", Microvascular Research 59, pp. 265-277, 2000.

A. Hempel, et al., "Atrial natriuretic peptide clearance receptor participates in modulating endothelial permeability", The American Physilogical Society, pp. H1818-H1825.

T. A. Desi, et al., Microfabricated Immunoisolating Biocapsules', Biotechnology and Bioengineering, vol. 57, No. 1, Jan. 5, 1998, pp. 118-120.

T. Murohara, et al., "Transplanted cord blood-derived endothelial precursor cells augment postnatal neovascularization", The Journal of Clinical Investigation, Jun. 2000, vol. 105, No. 11, pp. 1527-1536.

P. Carmeliet, et al., "Mechanism of angiogenesis and arteriogenesis", Nature Medicine, vol. 6, No. 3, Mar. 2000, pp. 389-395.

R. B. Vernon, et al., "A Novel, Quantitative Model for Study of Endothelial Cell Migration and Sprout Formation within Three-Dimensional Collagen Matrices", Microvascular Research 57, pp. 118-133, 1999.

V. Nehls, et al., "The Configuration of Fibrin Clots Determines Capillary Morphogenesis and Endothelial Cell Migration", Microvascular Research 51, pp. 347-364, 1996.

* cited by examiner

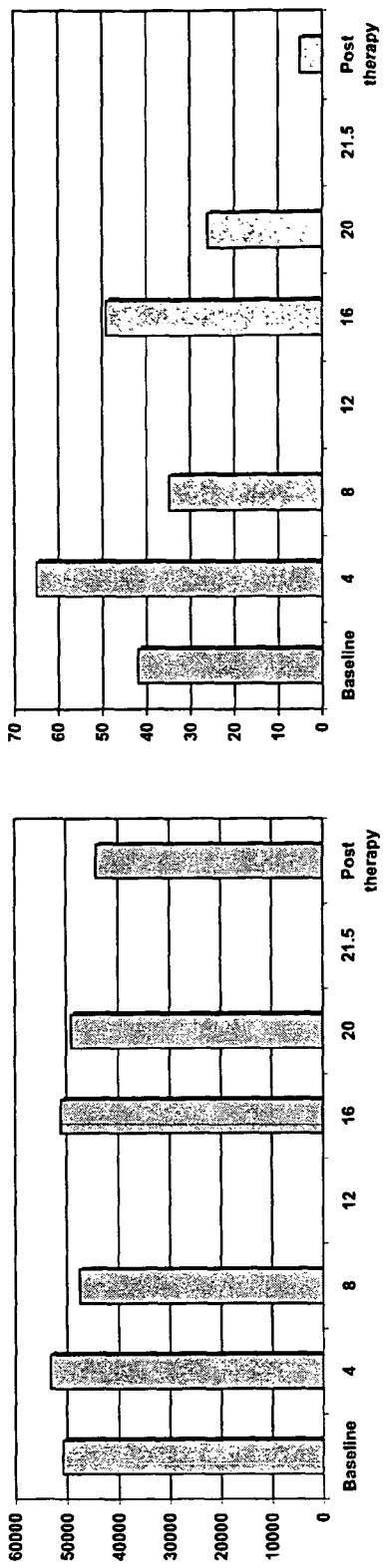
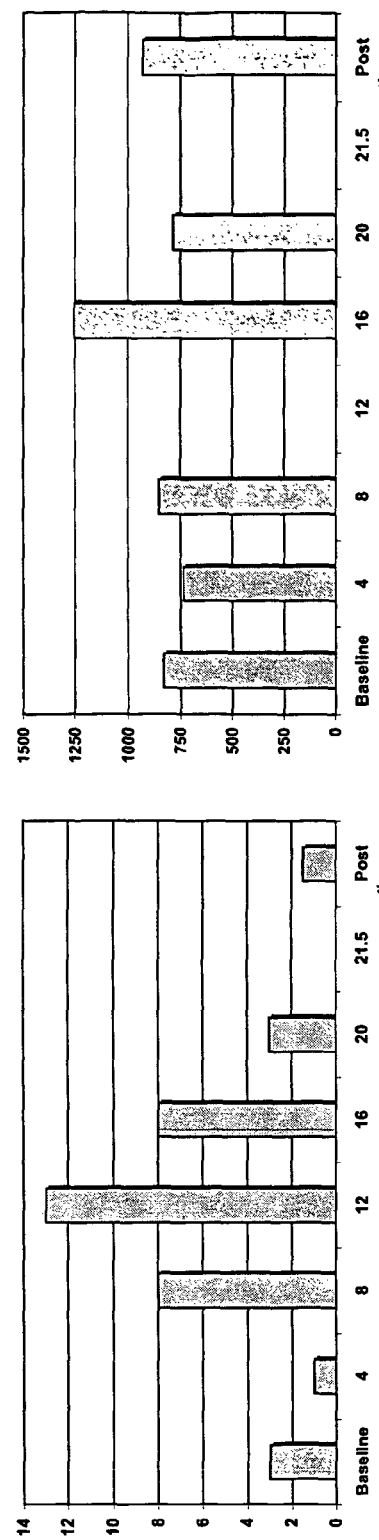
FIG. 5E FIG. 5F FIG. 5G FIG. 5H

RAD Phase I Patient CCF 001 Cytokine—Absolute Values

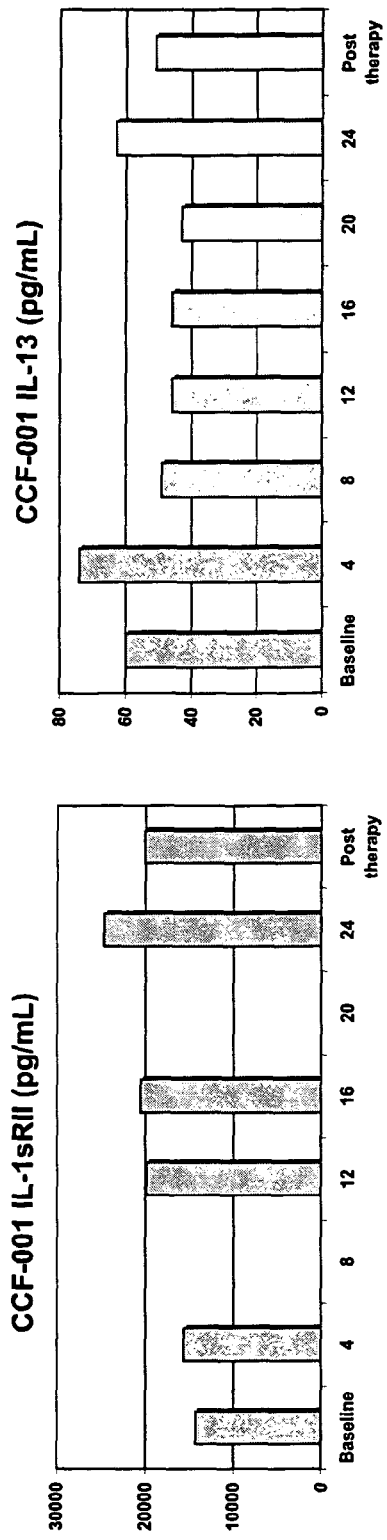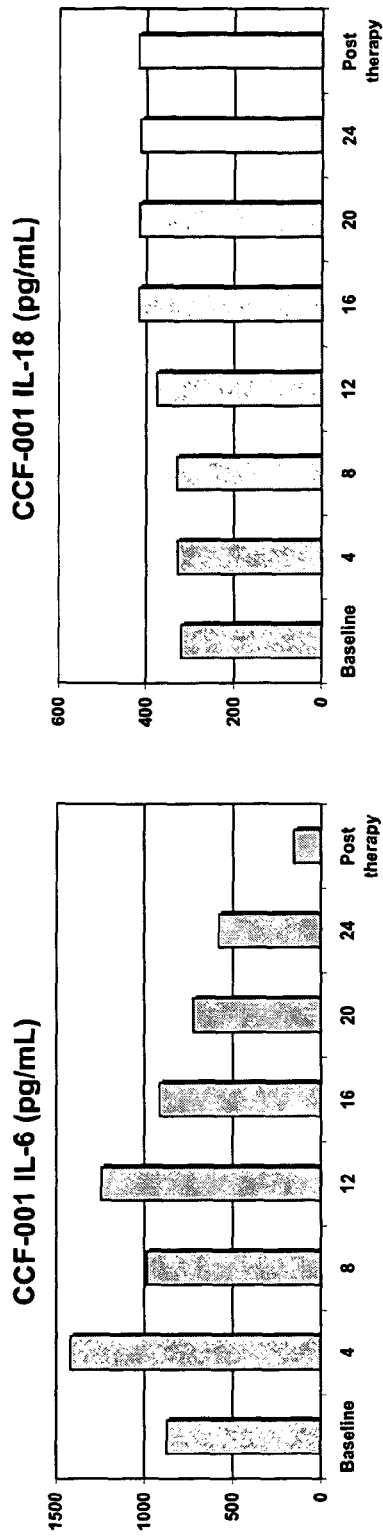
FIG. 8E  FIG. 8F  FIG. 8G  FIG. 8H

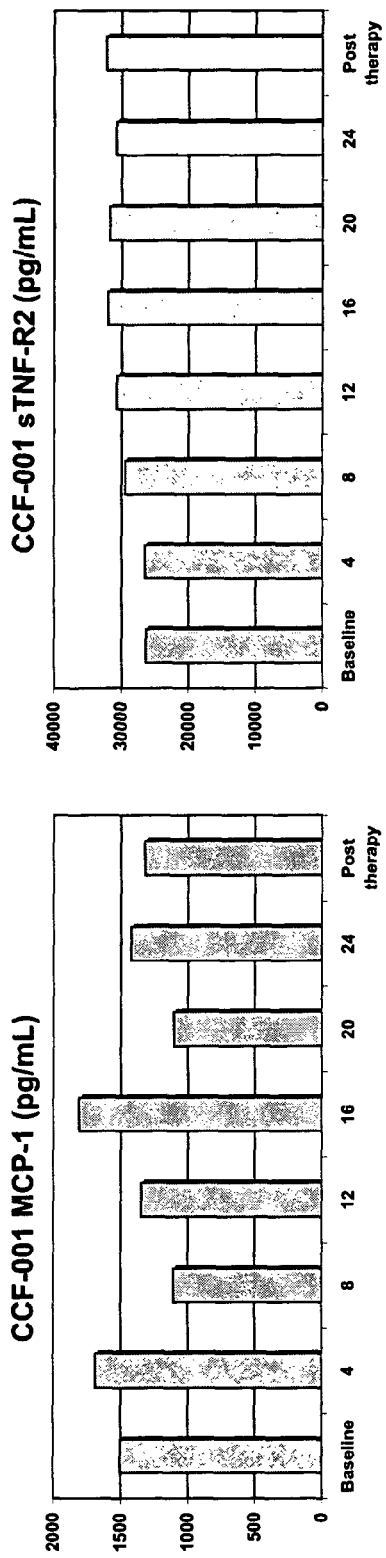
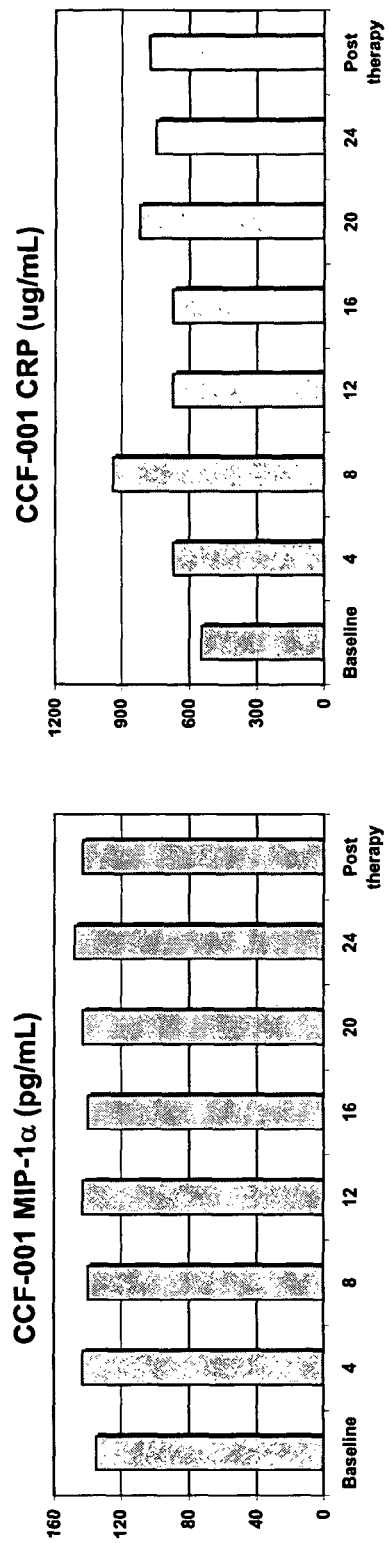
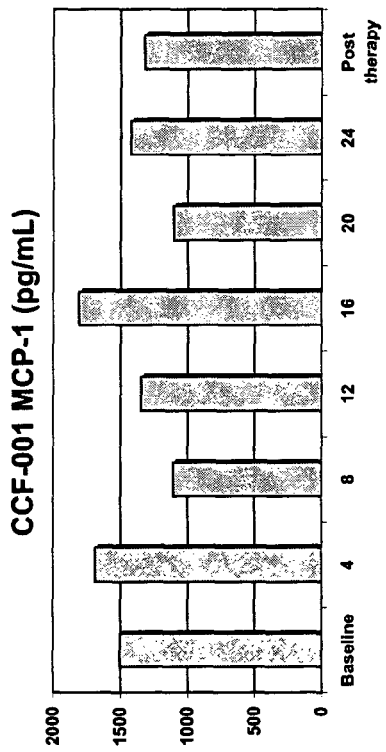
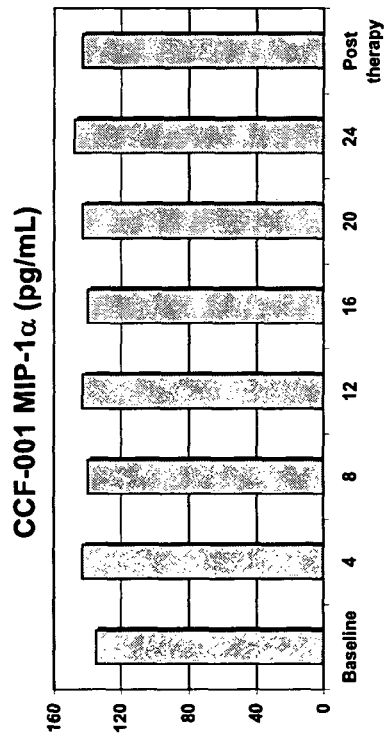
FIG. 8I
FIG. 8J
FIG. 8K
FIG. 8L

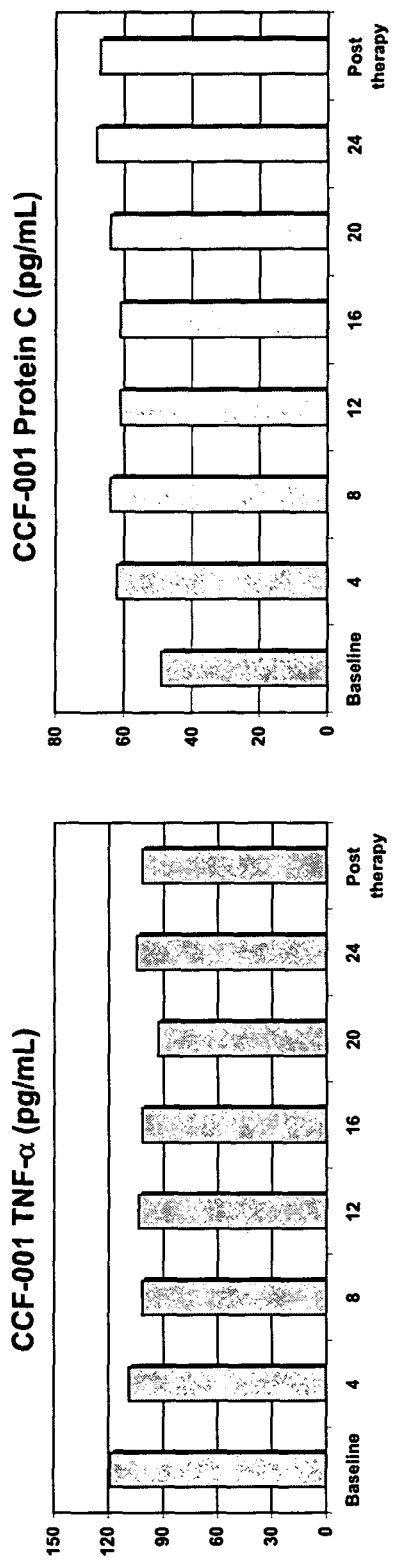

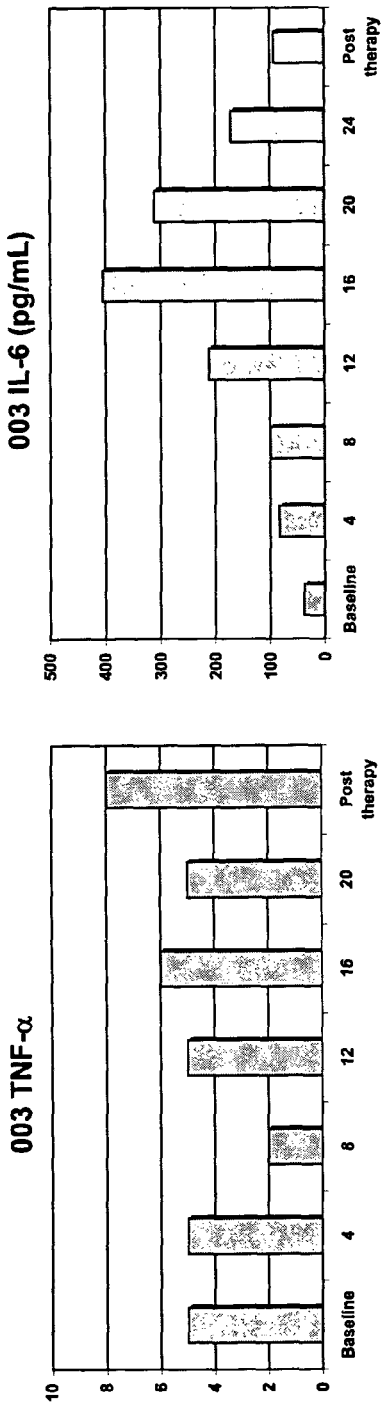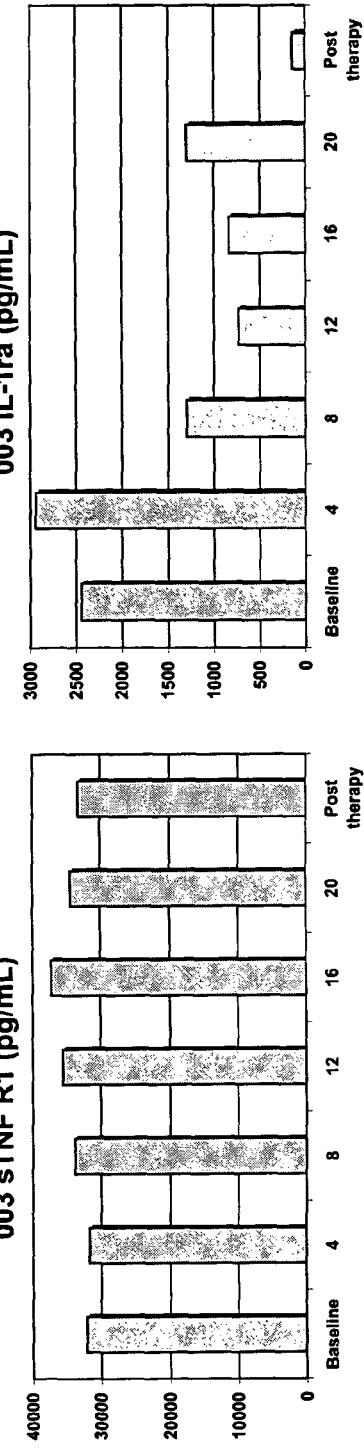
FIG. 14A
FIG. 14B
FIG. 14C
FIG. 14D

RAD Phase I/II Patient 003—Absolute Values
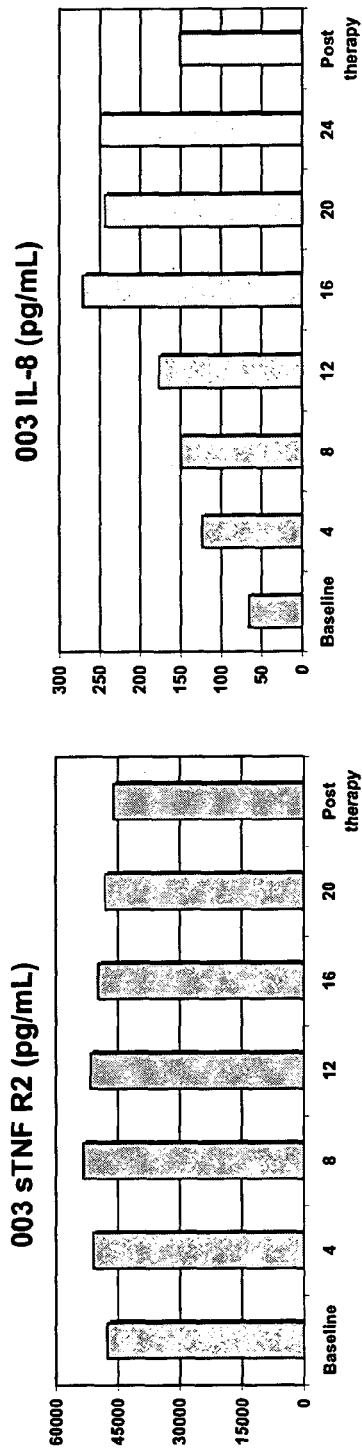
FIG. 14E
FIG. 14F
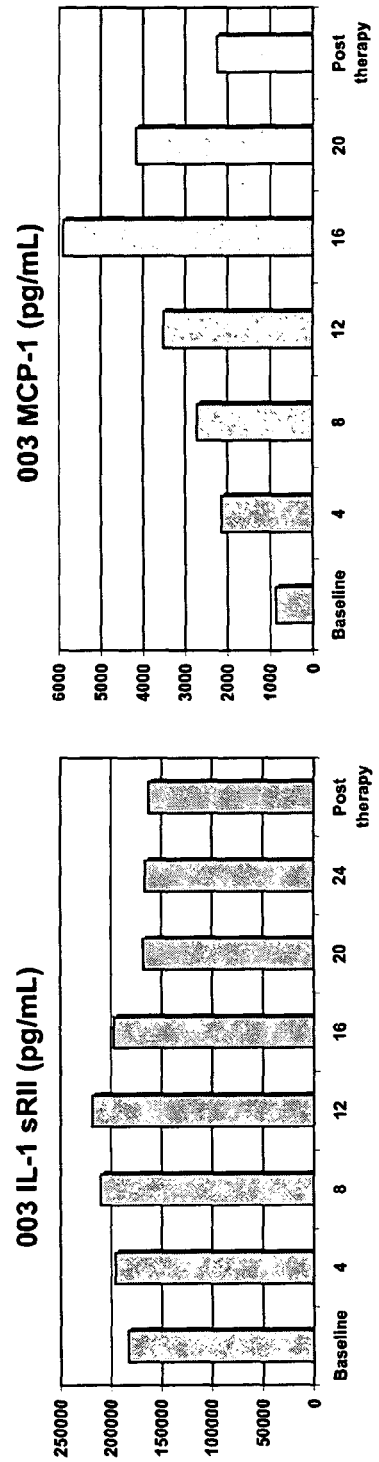
FIG. 14G
FIG. 14H

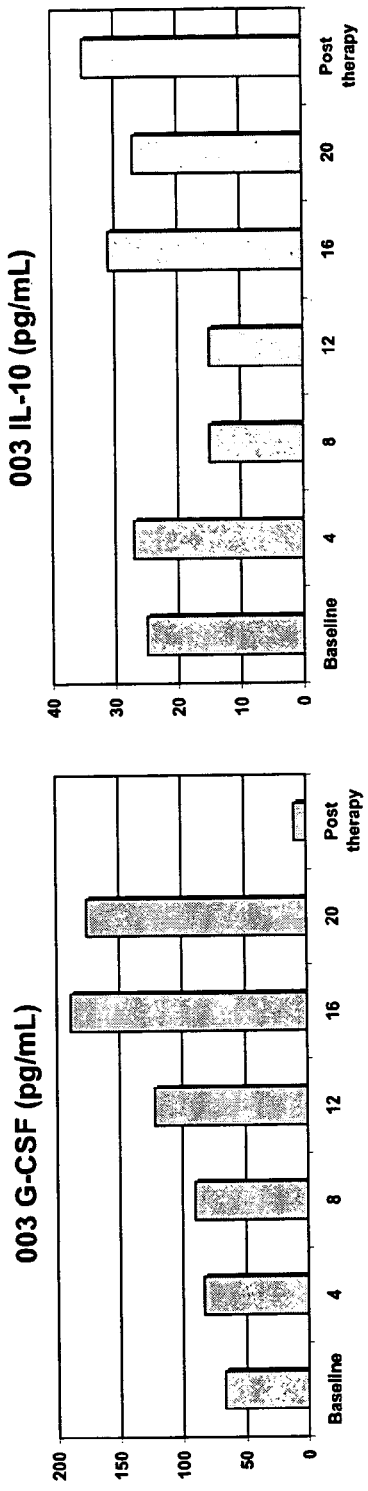
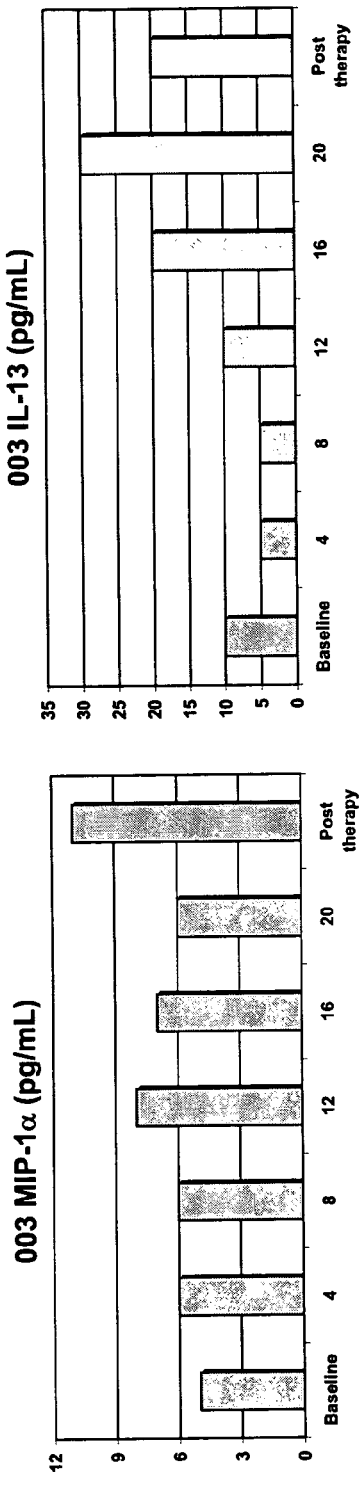
FIG. 14I  FIG. 14J  FIG. 14K  FIG. 14L

METHOD OF MODULATING INFLAMMATORY RESPONSE

BACKGROUND OF THE INVENTION

1. Field of the Invention

The present invention relates to a method for modulating inflammatory and pro-inflammatory states in a patient in need thereof by contacting the bodily fluid of the patient with renal tubule cells outside of the kidney.

2. Discussion of the Background

It is widely recognized that inflammatory cytokines play a role in the etiology of a variety of disease states, such as malnutrition, chronic congestive heart failure, inflammatory bowel disease, Crohn's disease, ulcerative colitis, rheumatoid arthritis, ankylosing spondylitis, systemic vasculitis, lupus, Wegener's granulomatosis, polyarteritis nodosa, dermatomyositis, diabetes mellitus Type I, thyroiditis, psoriasis, Guillian Barre syndrome, multiple sclerosis, and atherosclerosis, or other autoimmune disorders. [Refs. 1, 20, 21, 22, 23, 24, 25, 31, 32, 33, 34, 35, 36, 37, 38, 39]. Modulating the levels of such cytokines may provide a method of treating such patients. Accordingly, there remains a critical need for novel inflammation modulatory therapies for the treatment of patients suffering from, for example, at least one of the diseases discussed above.

Although maintenance dialysis therapy for end-stage renal disease (ESRD) has been used for almost 40 years, annual mortality rates among patients with ESRD undergoing hemodialysis remain greater than 20%. [Refs. 1, 2]. The most common cause of death in end-stage in ESRD patients (about 50%) is of cardiac or cardiovascular origin, with infection/sepsis (about 15%) being second. [Ref. 1].

The mortality from sepsis complicated by renal failure remains extremely high despite the application of modern renal replacement therapy. The systemic inflammatory response syndrome, or SIRS, is a catastrophic sequela of a variety of clinical insults, including infection, pancreatitis and cardiopulmonary bypass, and claims over a quarter million lives in the United States each year. [Refs. 3, 4, 5, 6, 7, 8].

The mortality is especially high in patients with multiple system organ failure syndrome (MSOF) and acute renal failure (ARF). The excess mortality seen in patients with sepsis and ARF is not ameliorated by conventional renal replacement therapy, which treats volume overload, uremia, acidosis, and electrolyte derangements. [Refs. 9, 6].

The prevalence of inflammation is high in dialysis patients; several lines of evidence suggest the presence of an ongoing acute-phase reaction in patients with ESRD undergoing hemodialysis. [Refs. 10, 11, 12]. Blood monocytes from hemodialysis patients are primed for cytokine production and predialysis serum contains elevated concentrations of inflammatory cytokines (for example, tumor necrosis factor-alpha [TNF-$\alpha$], interleukin-beta [IL-1$\beta$], interleukin-1, [IL-1], interleukin-6 [IL-6], interleukin-8 [IL-8], lipopolysaccharide biding protein, soluble lipopolysaccharide receptors [CD-14], GM-CSF, G-CSF, and chemokines) and anti-inflammatory cytokines (soluble TNF receptors [TNF-RI and TNF-RII], interleukin receptor antagonist [IL-1ra], interleukin-4 [IL-4], interleukin-10 [IL-10], interleukin-12 [IL-12], interleukin-13 [IL-13], and transforming growth factor-$\beta$ [TGF-$\beta$]). [Refs. 13, 14, 15, 16, 17, 30].

In fact, one of the strongest independent risk factors of mortality among patients undergoing hemodialysis is hypoalbuminemia. [Refs. 18, 19]. The generation of albumin is reduced and hypoalbuminemia develops as part of the acute phase response, mediated by proinflammatory cytokines (most directly interleukin-6 [IL-6]). [Ref. 2]. Accordingly, there remains an ongoing need for new methods for modulating the inflammatory response among hemodialysis patients.

SUMMARY OF THE INVENTION

It is an object of the present invention to provide methods of modulating the levels of at least one inflammatory cytokine in a patient in need thereof.

It is another object of the present invention to provide methods for increasing the level of at least one inflammatory cytokine in the patient.

It is another object of the present invention to provide methods for decreasing the level of at least one inflammatory cytokine in the patient.

It is another object of the present invention to provide methods of treating hemodialysis patients suffering from ESRD, chronic renal insufficiency (CRI), SIRS, ARF, or sepsis by modulating the inflammatory response, by modulating the levels of inflammatory cytokines.

It is another object of the present invention to provide methods of treating non-renal diseases which are associated with a suppressed or stimulated inflammatory response. These diseases include malnutrition, chronic congestive heart failure, inflammatory bowel disease, Crohn's disease, ulcerative colitis, rheumatoid arthritis, ankylosing spondylitis, systemic vasculitis, lupus, Wegener's granulomatosis, polyarteritis nodosa, dermatomyositis, diabetes mellitus Type I, thyroiditis, psoriasis, Guillian Barre syndrome, multiple sclerosis, and atherosclerosis.

The present invention is based, in part, on the discovery that modulation of inflammatory cytokines can be used to treat a patient in an acute or chronic inflammatory state. Such a patient may be suffering from ESRD, chronic renal insufficiency (CRI), SIRS, ARF, or sepsis. This treatment method includes contacting a body fluid with renal tubule cells outside of the kidney As a result of this contact, the tubule cells introduce mediators into and/or reabsorb mediators from the body fluid. After contact with the tubule cells, at least a portion of the body fluid is recirculated to the patient, where the presence of mediators introduced to the body fluid or the absence of mediators due to reabsorption induce a response in the patient, which leads to amelioration of the inflammatory state by modulation of the inflammatory cytokines.

Accordingly, the objects of the present invention, and others, may be accomplished with a method of treating a patient in an acute or chronic inflammatory state by modulating the levels of the inflammatory cytokines, comprising:

contacting, outside of the kidney, at least a portion of a body fluid of the patient with renal tubule cells.

The objects of the present invention, and others, may also be accomplished with a method of treating a patient in an acute inflammatory state by modulating the levels of the inflammatory cytokines, comprising:

removing a portion of body fluid from the patient, contacting the removed body fluid with renal tubule cells, and returning at least a portion of the body fluid, which has been, contacted with the renal tubule cells to the patient.

The objects of the present invention may also be achieved by enhancing at least one inflammatory cytokine, where the inflammatory cytokine may be either a proinflammatory cytokine or an anti-inflammatory cytokine.

The objects of the invention may also be achieved by suppressing at least one inflammatory cytokine, where the inflammatory cytokine may be either a proinflammatory cytokine or an anti-inflammatory cytokine.

In this respect, examples of proinflammatory cytokines include tumor necrosis factor-alpha [TNF-α], interleukin-beta [IL-1β], interleukin-1, [IL-1], interleukin-6 [IL-6], interleukin-8 [IL-8], lipopolysaccharide-biding protein, soluble lipopolysaccharide receptors [CD-14], GM-CSF, G-CSF, and chemokines.

In this respect, examples of anti-inflammatory cytokines include soluble TNF receptors [TNF-RI and TNF-RII], interleukin receptor antagonist [IL-1ra], interleukin-4 [IL-4], interleukin-10 [IL-10], interleukin-12 [IL-12], interleukin-13 [IL-13], and transforming growth factor-β [TGF-β].

In a preferred embodiment, the above-stated objects may be obtained by contacting the body fluid with the renal tubule cells ex vivo.

Another embodiment of the present invention involves contacting the body fluid with the renal tubule cells inside the body of the patient.

A preferred embodiment of the present invention is the enhancement of at least one inflammatory cytokine by contacting a body fluid with renal tubule cells outside of the kidney, where the inflammatory cytokine may be either a proinflammatory cytokine or an anti-inflammatory cytokine.

In another embodiment of the present invention, at least one inflammatory cytokine may be suppressed by contacting a body fluid with renal tubule cells outside of the kidney, where the inflammatory cytokine may be either a proinflammatory cytokine or an anti-inflammatory cytokine.

The above objects highlight certain aspects of the invention. Additional objects, aspects and embodiments of the invention are found in the following detailed description of the invention.

BRIEF DESCRIPTION OF THE FIGURES

A more complete appreciation of the invention and many of the attendant advantages thereof will be readily obtained as the same becomes better understood by reference to the following Figures in conjunction with the detailed description below.

FIG. 14: Plasma cytokine levels relative to baseline pre-therapy levels. Absolute values are summarized in Table 3.

DETAILED DESCRIPTION OF THE INVENTION

Figure 1:
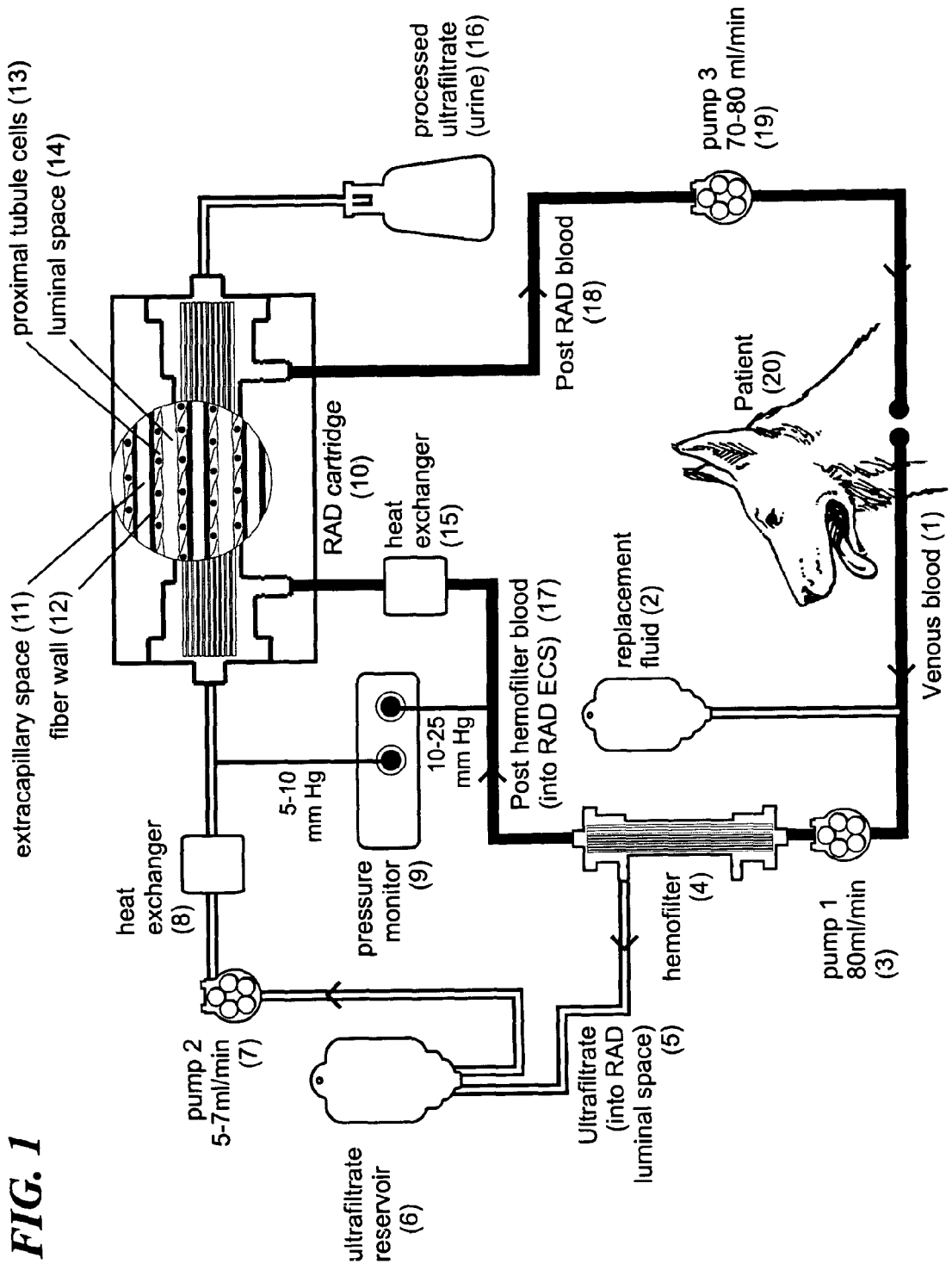
FIG. 1: RAD perfusion chart.

Unless specifically defined, all technical and scientific terms used herein have the same meaning as commonly understood by a skilled artisan in biochemistry, cellular biology, molecular biology, and the medical sciences.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will control. Further, the materials, methods, and examples are illustrative only and are not intended to be limiting, unless otherwise specified.

The present invention is based, in part, on the discovery that modulation of inflammatory cytokines can be used to treat a patient in an inflammatory state. Such a patient may be suffering from ESRD, chronic renal insufficiency (CRI), SIRS, ARF, or sepsis. A further description of SIRS is provided by U.S. patent application Ser. No. 09/941,987 filed Aug. 30, 2001, which is incorporated herein by reference in its entirety.

This treatment method includes contacting a body fluid with renal tubule cells outside of the kidney. Without being limited to any particular theory, it is believed that as a result of this contact, the tubule cells introduce mediators into the body fluid and/or reabsorb mediators from the body fluid. After contact with the tubule cells, at least a portion of the body fluid is recirculated to the patient, where the presence of mediators introduced to the body fluid or the absence of mediators due to reabsorption induce a response in the patient, which leads to amelioration of the inflammatory state by modulation of the inflammatory cytokines.

As will be readily appreciated by one skilled in the art, the renal disorders ESRD, chronic renal insufficiency (CRI), SIRS, ARF, or sepsis differ in their etiology, individual cytokine response, and treatment regimen. However, these disorders share a relationship involving a acute inflammatory state. Accordingly, a method of modulating the cytokine response levels thereby ameliorating the associated disorder would be of tremendous importance in the medical field.

However, the need for modulating the levels of inflammatory cytokines is not limited to patients on hemodialysis or suffering a renal ailment. It has been widely recognized that inflammatory cytokines play a role in the etiology of malnutrition, chronic congestive heart failure, inflammatory bowel disease, Crohn's disease, ulcerative colitis, rheumatoid arthritis, ankylosing spondylitis, systemic vasculitis, lupus, Wegener's granulomatosis, polyarteritis nodosa, dermatomyositis, diabetes mellitus Type I, thyroiditis, psoriasis, Guillian Barre syndrome, multiple sclerosis, and atherosclerosis, as well as other autoimmune disorders. [Refs. 1, 20, 21, 22, 23, 24, 25, 31, 32, 33, 34, 35, 36, 37, 38, 39].

The inventor has discovered that an element of amelioration of the aforementioned disorders is that when the body fluid is contacted with the renal tubule cells, the cytokine response and hemodynamics of animals are affected. Accordingly, the renal tubule cells provide an immunomodulatory effect. This effect is most notably achieved by modulating inflammatory cytokine expression, either by stimulating or suppressing expression thereof.

The inventive method involves contacting, outside of the kidney, at least a portion of the body fluid of the patient with renal tubule cells. A preferred embodiment of the present invention is the enhancement of at least one inflammatory cytokine by contacting a body fluid with renal tubule cells outside of the kidney, where the inflammatory cytokine may be either a proinflammatory cytokine or an anti-inflammatory cytokine.

In another embodiment of the present invention, at least one inflammatory cytokine may be suppressed by contacting a body fluid with renal tubule cells outside of the kidney, where the inflammatory cytokine may be either a proinflammatory cytokine or an anti-inflammatory cytokine.

In another embodiment of the invention, the object of modulating the levels of inflammatory cytokines can be achieved by removing a portion of body fluid from the patient, then contacting the removed body fluid with renal tubule cells, and subsequently returning at least a portion of the body fluid which has been contacted with the renal tubule cells to the patient.

The method of the present invention may provide for enhancing the levels of at least one inflammatory cytokine, where the inflammatory cytokine may be either a proinflammatory cytokine or an anti-inflammatory cytokine. Alternatively, the method of the present invention may provide for suppressing the levels of at least one inflammatory cytokine, where the inflammatory cytokine may be either a proinflammatory cytokine or an anti-inflammatory cytokine.

Known examples of proinflammatory cytokines include, but are not limited to, tumor necrosis factor-alpha [TNF-α], interleukin-beta [IL-1β], interleukin-1, [IL-1], interleukin-6 [IL-6], interleukin-8 [IL-8], lipopolysaccharide-biding protein, soluble lipopolysaccharide receptors [CD-14], GM-CSF, G-CSF, and chemokines.

Known examples of anti-inflammatory cytokines include, but are not limited to, soluble TNF receptors [TNF-RI and TNF-RII], interleukin receptor antagonist [IL-1ra], interleukin-4 [IL-4], interleukin-10 [IL-10], interleukin-12 [IL-12], interleukin-13 [IL-13 ], and transforming growth factor-β [TGF-β].

Modulation of inflammatory cytokines can be assessed by determining the level (reported in pg/ml) of each cytokine in the plasma or by measuring the level of expression of the cytokines in the blood cells. Plasma cytokine levels can be determined, for example, by utilizing a cytokine detection kit. One such kit is manufactured and distributed by R & D Systems, Inc. (Minneapolis, Minn.). Expression levels of cytokine genes in the blood cells may be determined, for example, by microarray analysis. One skilled in the art may find technical guidance for microarray techniques in the recent review by John Quackenbush [Ref. 40].

The patient may be a human or a non-human animal, such as a mammal. Exemplary non-human animals include dogs, cats, horses, cows, sheep, goats, and pigs. Human patients are especially preferred.

A feature of the present invention is that the body fluid of the patient is contacted with renal tubule cells. It is important to note that the body fluid of the patient is contacted with renal tubule cells outside of the kidney. In the present invention, the natural flow of the body fluid is interrupted so that the fluid can interact with the renal tubule cells. After this contact, the body fluid is returned to the course of natural flow in the patient's body. Thus, the present invention is distinct from the natural physiological processes, which occur in the kidney.

Methods and devices for contacting a body fluid with renal tubule cells and then returning the treated fluid to the patient are well known in the art. See, for example, references 26, 27, 28, 29, and U.S. Pat. No. 6,150,164, all of which are incorporated herein by reference in their entirety. In a particularly preferred embodiment of the invention, the body fluid of the patient is contacted in with the renal tubule cells in a renal tubule assist device (RAD). As used herein, the term "renal tubule assist device" refers to a device, which contains (1) renal tubule cells and (2), an inlet and outlet for the body fluid, where the body fluid is contacted with the renal tubule cells inside the device. Such a device is described in detail in the publications cited immediately above. An example of a suitable RAD is shown in FIG. 1 as element (10) in the circuit shown therein.

In addition to the methods described in the publications cited immediately above, the renal tubule cells may also be grown on solid or porous microcarrier beads. Examples of suitable microcarrier beads include micropourous gelatin and collagen-coated dextran. In this embodiment, the cells can be grown on the beads. Then, the cells can be detached from the beads and be seeded in the RAD. In another embodiment, the cells on the beads can be used in the extracapillary space of a sepsis-treating cartridge on microcarrier beads as opposed to single monolayers along the inner surface of hollow fibers. Thus, a body fluid of a patient could be perfused into a cartridge containing these cells in this formulation for exposure to the patient's fluid and respond with mediators that would modulate the levels of the inflammatory cytokines.

The tubule cells may be obtained from a human or a non-human animal source. The non-human animal is preferably a mammal. Suitable examples of non-human cells are porcine, rat, dog, mouse, or rabbit tubule cells. Transformed tubule cells may also be used in the present invention. Such cells are described in, for example, U.S. Pat. No. 6,150,164.

The body fluid may be blood, plasma, or ultrafiltrate of plasma. Venous blood is particularly preferred. Arterial blood may also be used.

In one embodiment of the invention, the body fluid of the patient is contacted in with the renal tubule cells ex vivo, i.e, outside of the body of the patient. In an alternative embodiment, the body fluid is contacted in with the renal tubule cells inside the body of the patient.

In one embodiment, the renal tubule assist device is ex vivo. Alternatively, the renal tubule assist device is implanted in the patient.

In another embodiment, the implanted renal tubule cells may be contained within a cell cartridge, which may be implanted into an intact blood vessel. An example of a device that can be implanted is described in, for example, U.S. Pat. No. 5,704,910 and U.S. Pat. No. 5,911,704, the entire contents of both of these patents are incorporated herein by reference in their entirety.

The patient may also be afflicted with renal disease, for example acute renal failure or chronic renal failure. Such a patient may be afflicted with end-stage renal disease. The patient may also be septic. Such a patient may also be on hemo- or peritoneal dialysis. Further, the patient may be suffering from malnutrition, chronic congestive heart failure, inflammatory bowel disease, Crohn's disease, ulcerative colitis, rheumatoid arthritis, ankylosing spondylitis, systemic vasculitis, lupus, Wegener's granulomatosis, polyarteritis nodosa, dermatomyositis, diabetes mellitus Type I, thyroiditis, psoriasis, Guillian Barre syndrome, multiple sclerosis, and atherosclerosis.

An example of a specific embodiment of the present invention is shown in FIG. 1. In this embodiment, venous blood (1) from the patient (20) afflicted with sepsis is removed. The removed blood (1) is sent via pump (3) to hemofilter (4). Replacement fluid (2) is added to the venous blood (1) during transport to hemofilter (4). From hemofilter (4), the ultrafiltrate (5) is passed to ultrafiltrate reservoir (6) and the post hemofilter blood (17) is sent to the RAD cartridge (10) after passing through heat exchanger (15). The ultrafiltrate is transferred to the RAD cartridge (10) via pump (7) and heat exchanger (8). Pressure monitor (9) is used to monitor the pressure in the input flows to cartridge (10). Cartridge (10) comprises extracapillary space (11), fiber wall (12), proximal tubule cells (13), and luminal space (14). Post RAD blood (18) is then transferred via pump (19) back to patient (20). The processed ultrafiltrate (16) is collected from the RAD cartridge (10).

Having generally described this invention, a further understanding can be obtained by reference to certain specific examples, which are provided herein for purposes of illustration only, and are not intended to be limiting unless otherwise specified.

EXAMPLES

Example 1

Treatment of a Human Patient Afflicted with Sepsis with Renal Tubule Cells

A 29 year-old man presented to the emergency room with a one-day history of nausea, vomiting, diarrhea, chills and fever. The morning of admission he noted redness, swelling and pain in his right thigh. Over the subsequent four hours the redness, swelling and pain extended to his calf. Upon presentation, the patient had a temperature of 103.5° F., and blood pressure of 101/42. Bibasilar rates were noted. His right thigh and calf were erythematous, swollen and tender. On admission, his white blood count was 20,200 with a marked left shift, and his platelet count was 174,000. His serum electrolytes were normal, but his serum creatinine was 2.9 mg/dl and BUN 38 mg/dl. His arterial blood gases on 3 L nasal cannula was pH 7.46 $pCO_2$ 32 mm Hg, $pO_2$ 65 mm Hg. Chest x-ray showed no infiltrates. Blood cultures were obtained, ceftriaxone 2 gm and clindamycin 900 mg were given intravenously. A CT scan of his right leg revealed no gas, fluid collections or necrotizing tissue.

After slight improvement over the first 24 hours, his condition began to rapidly deteriorate with shortness of breath, oliguria and hypotension. Repeat plasma chemistry values revealed rising liver function tests with alanine amino transferase (ALT) 155 IU/1, aspartate amino transferase (AST) 189 IU/1, total bilirubin 4.1 mg/dl, serum creatinine 7.6 mg/dl, BUN 69 mg/dl, calcium 6.8 mg/dl and a creatinine phosphokinase 460 IU/1. Arterial blood gases on 6 L nasal cannula were pH 7.23, $pCO_2$ 40 mm Hg, $pO_2$ 68 mm Hg. Chest x-ray revealed multilobar infiltrates. A clinical diagnosis of streptococcal toxic shock syndrome was made and intravenous antibiotics were continued with ceftriaxone 2 gm q8h, clindamycin 900 mg q8h and a single dose of vancomycin, 1.5 gm. He was transferred to the intensive care unit approximately 24 hours after admission and intubated to maintain adequate oxygenation attaining a $pO_2$ of 68 mm Hg with $F_iO_2$ of 60 percent. His blood cultures were reported positive for beta hemolytic streptococcus Group A. Emergent surgical exploration of his left calf revealed no necrotizing fasciitis or myonecrosis, which was confirmed on histologic evaluation. Tissue specimens from the procedure were also culture positive for beta-hemolytic streptococcus Group A.

After returning from surgery, now 36 hours after admission, his condition continued to deteriorate with worsening hypotension to 68/42 requiring vasopressor support with dopamine, phenylephrine, and levarterenol. He was started on continuous venovenous hemofiltration to treat his acute renal failure. Over the subsequent 72 hours, his liver function tests elevated to a high of ALT 904, AST 1404, total bilirubin 5.6 mg/dl, creatinine phosphokinase 45,530, and lows of serum calcium 5.9 mg/dl, serum albumin 1.8 mg/dl, hematocrit 29.5 percent, platelet count 28,000. During this critical period, his cardiac output was markedly elevated between 9-12 L/min and his systemic vascular resistance varied between 300-500.

Because of his worsening condition, the patient was considered to be included in a Phase I/II clinical trial at The University of Michigan to test the safety and functionality of a bioartificial kidney. Pre-clinical large animal experiments have suggested that this device can ameliorate the cardiovascular consequences of septic shock in uremic animals. This study is an investigator-initiated trial reviewed and approved by the U.S. Food and Drug Administration (FDA) and be the local institutional review board (IRB). The patient met all inclusion and exclusion criteria of the protocol and his family agreed to allow him to participate in the study and signed a detailed informed consent document.

The bioartificial kidney is comprised of a continuous venovenous hemofiltration (CVVH) circuit connected to a synthetic hemofiltration cartridge, and a Renal Tubule Assist Device (RAD). The RAD is a commercial hemofiltration cartridge (Fresenius F40, Fresenius AG, Bad Hamburg, Germany) in which human renal tubule cells have been grown to confluence along the inner surface of the hollow fibers. The human cells were isolated and expanded from human kidneys obtained from the National Disease Research Interchange (NDRI, Arlington, Va., USA). NDRI is a not-for-profit organization and provides tissues and organs originally retrieved for transplant, but due to donor/recipient incompatibility, transplantation is not possible. A written informed consent document was obtained for each kidney donor and is kept on file at the tissue acquisition site.

After 36 hours of CVVH, the bioartificial kidney replaced the hemofiltration cartridge in the extracorporeal circuit. A variety of physiologic parameters of the patient were carefully monitored prior to, during and after the use of the biohybrid device. Key parameters are summarized in FIGS. 2-4.

Figure 2:
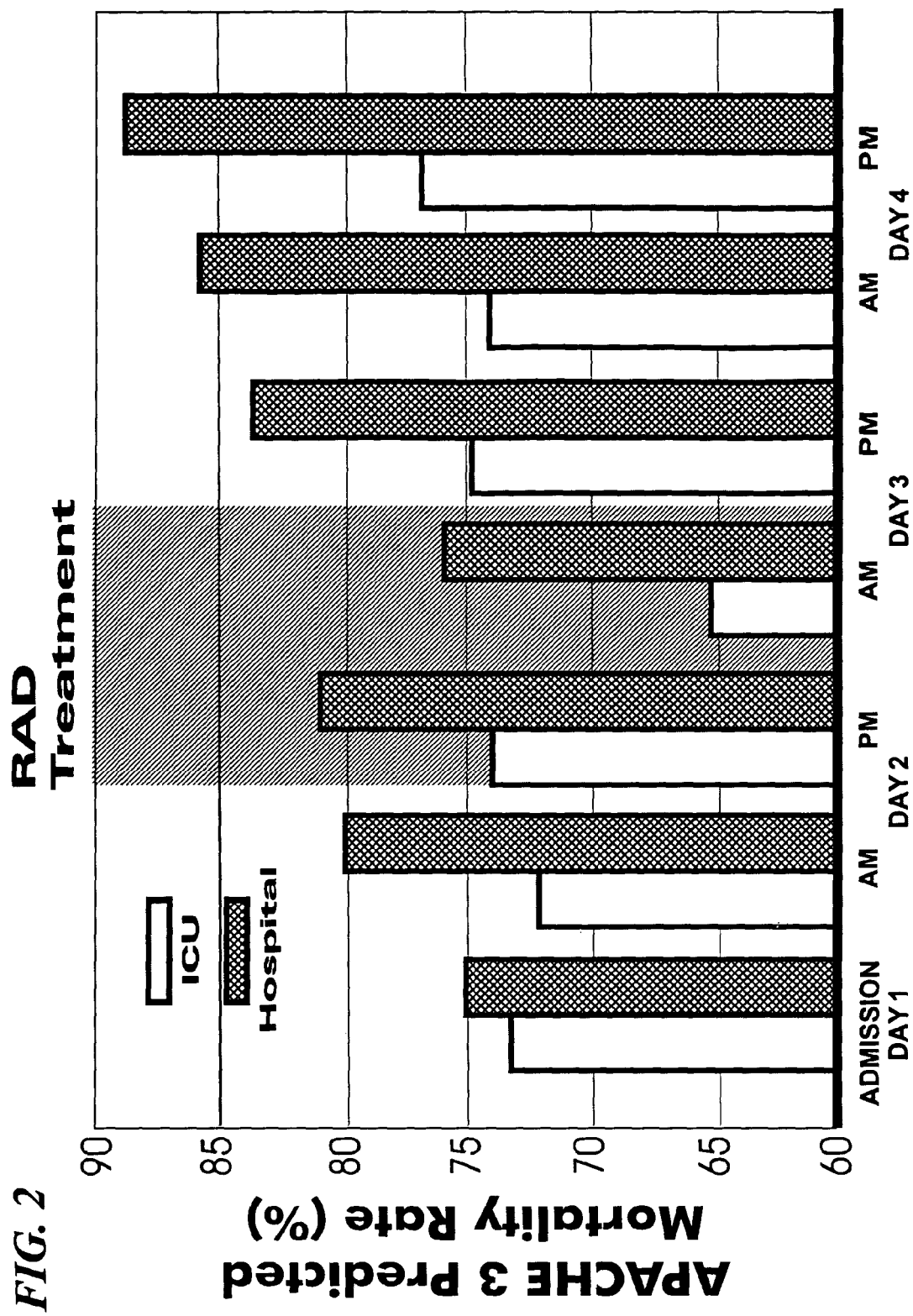
FIG. 2: Patient's predicted mortality rates from daily Apache 3 scoring in the medical ICU. The AM rate is an 8 AM Apache 3 score using the parameters of the patient at that hour of the day. The PM rate is determined by compiling the worst score in each parameter during the patient's 24 hour ICU stay from midnight (0000 hours) the preceding day to the following midnight (2359 hours).

As displayed in FIG. 2, the patient's Apache 3 score and predicted ICU and in hospital mortality rate was dramatically reduced during RAD treatment. The AM score was assessed after 16 hours of RAD therapy. These predicted mortality rates during RAD treatment were substantially lower, compared to the prior and following day (AM and PM) values. The RAD was discontinued after 21.5 hours of use due to a prior determined termination event of a platelet count lower than 35,000 for safety reasons.

Figure 3:
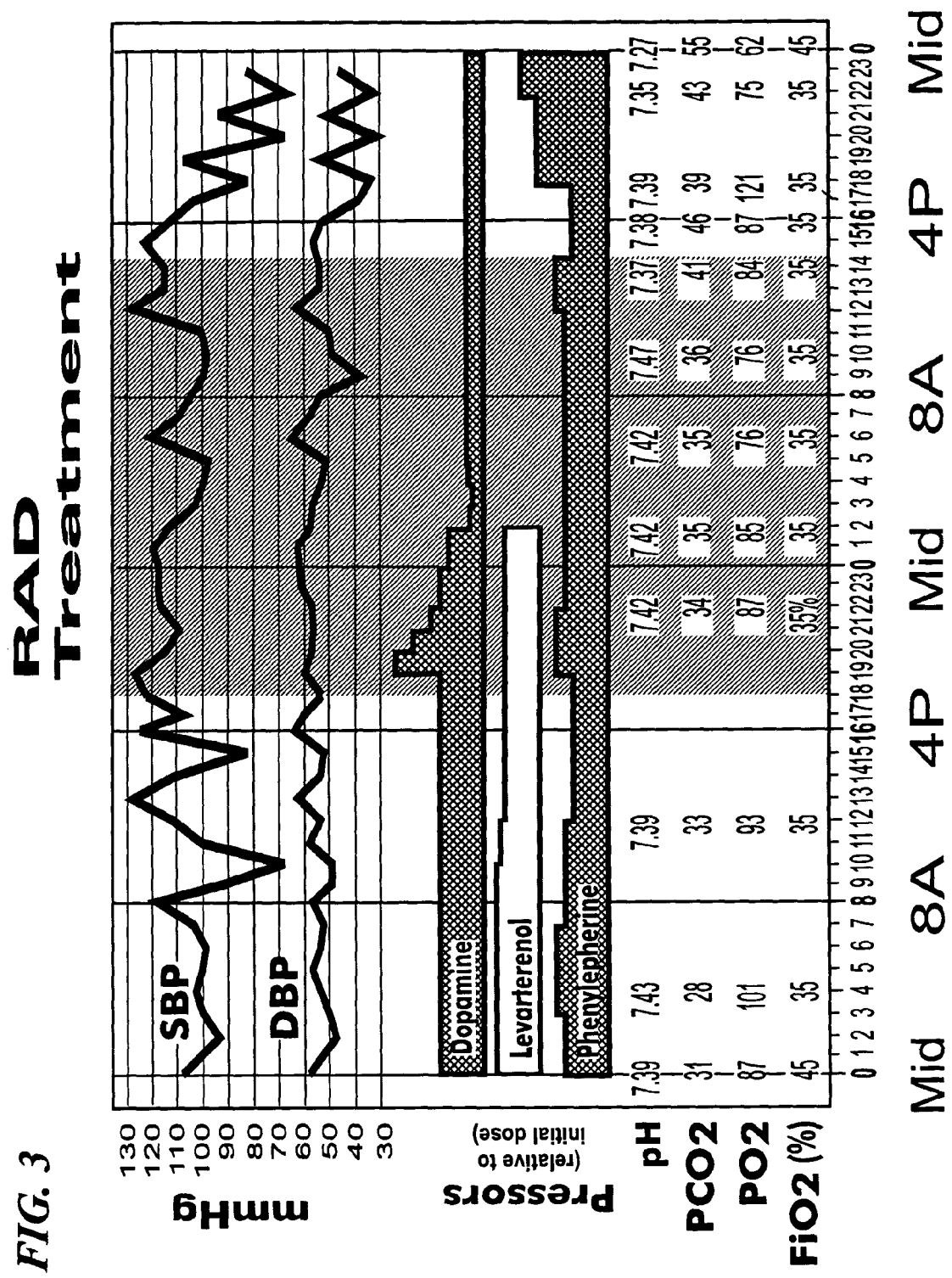
FIG. 3: Blood pressures, vasopressor dosage and arterial blood gases in relation to fractional inspired oxygen ($F_iO_2$) with time in the patient. The pressor dosage is presented as relative to the dose at the beginning (midnight, 0000 hour) of the time period. The beginning dosages were the following: dopamine (5 ug/kg/min), phenylepherine (1.5 ug/kg/min) and levarterenol (0.2 ug/kg/min).
Figure 4:
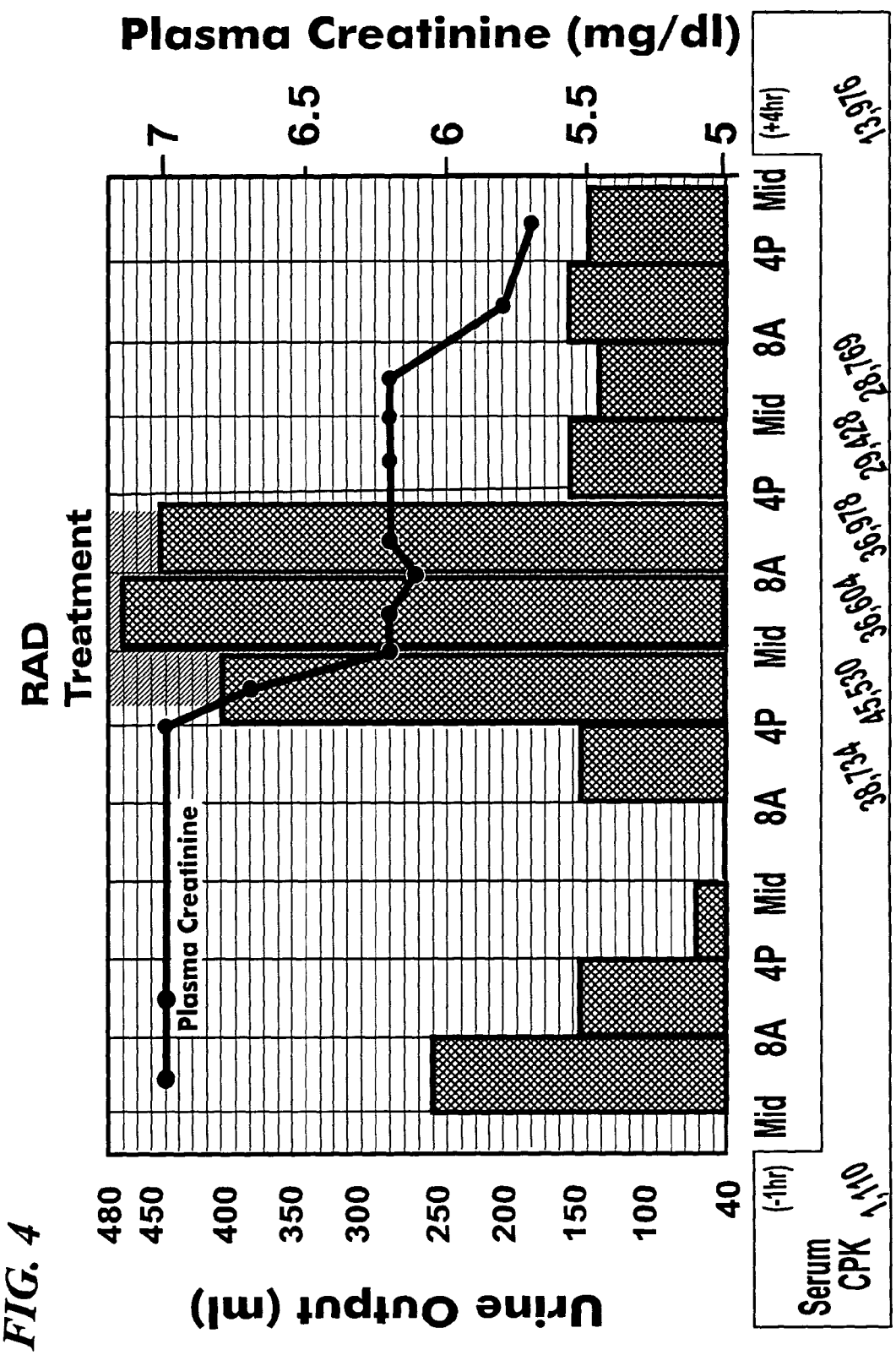
FIG. 4: The time course of urine output (left scale) and plasma creatinine concentration (right scale) in the patient. The plasma CPK levels (IU/l) are also displayed along the bottom panel.
Figure 5B:
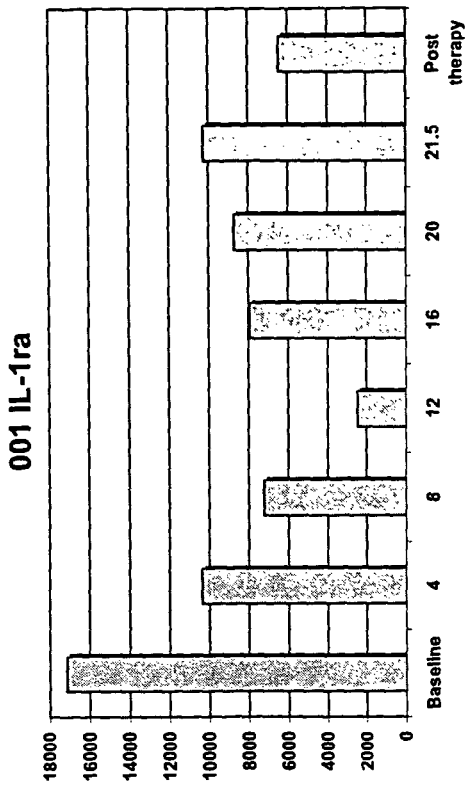
FIG. 5: Plasma cytokine levels relative to baseline pre-therapy levels. Absolute values are summarized in Table 1.
Figure 5D:
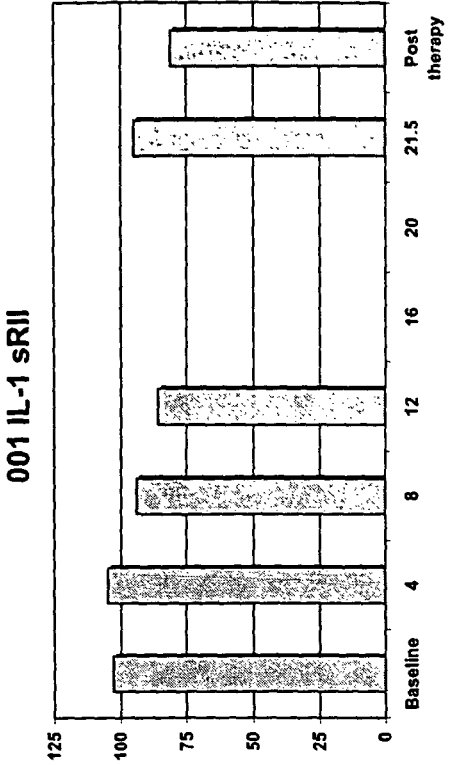
Figure 5A:
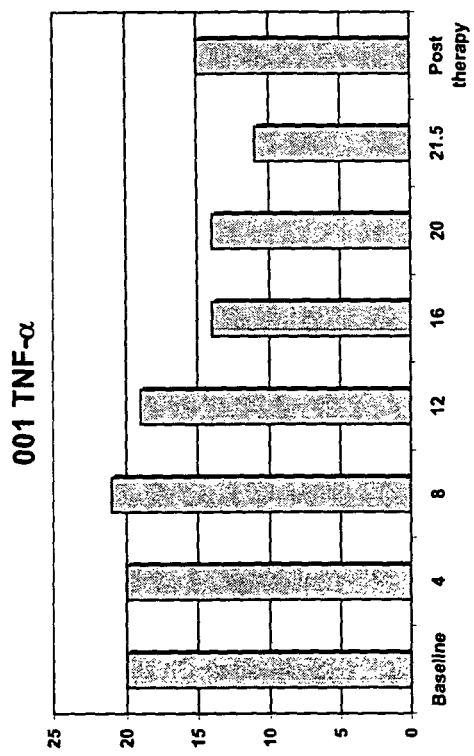
Figure 5C:
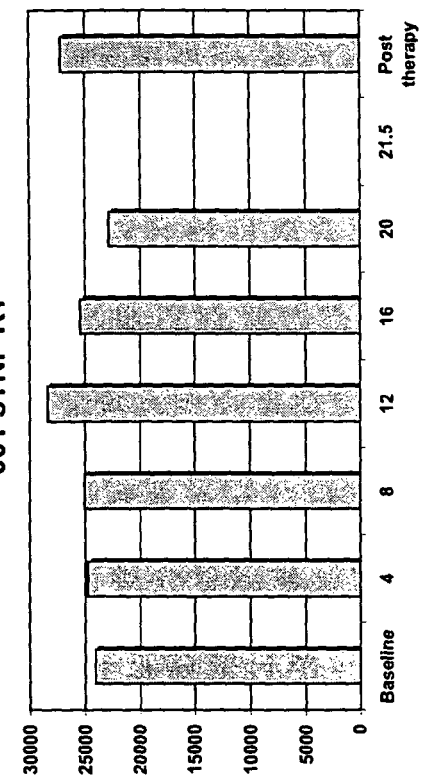
Figure 5J:
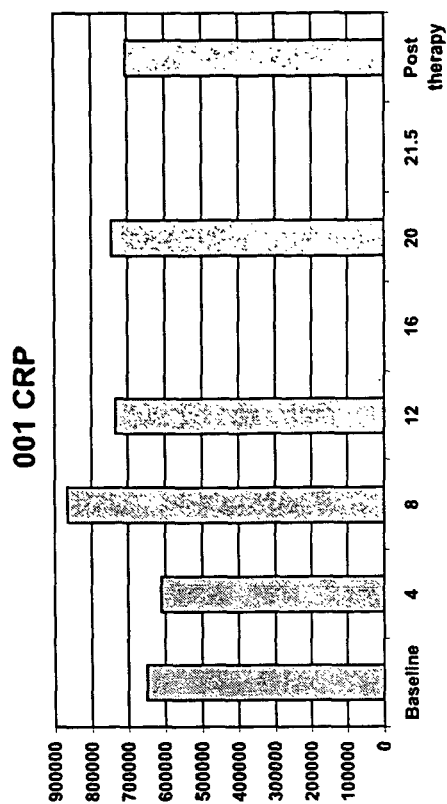
Figure 5L:
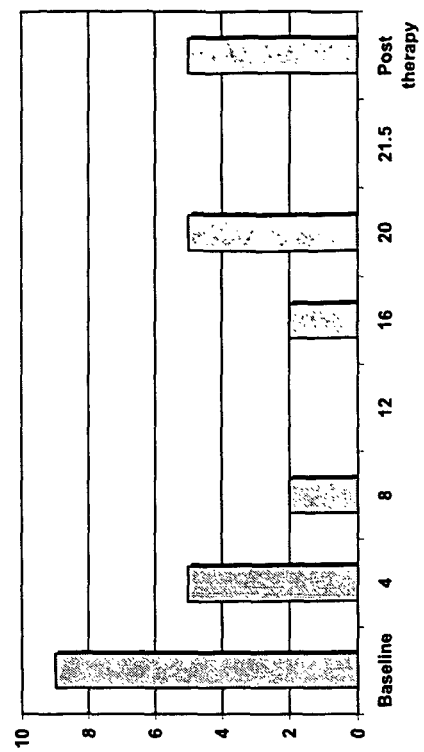
Figure 5I:
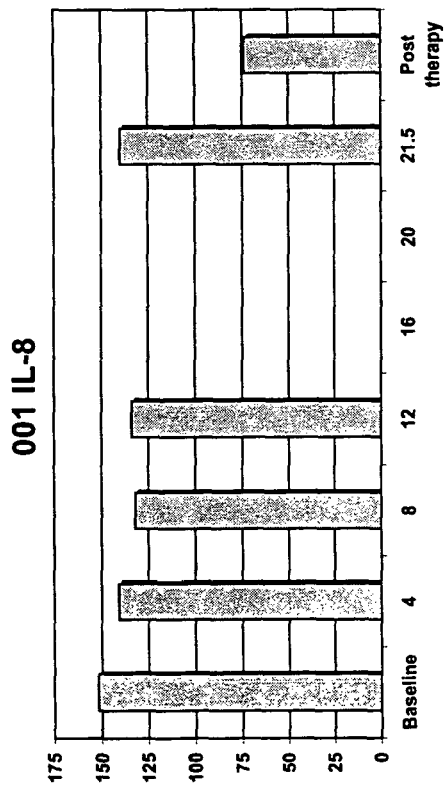
Figure 5K:
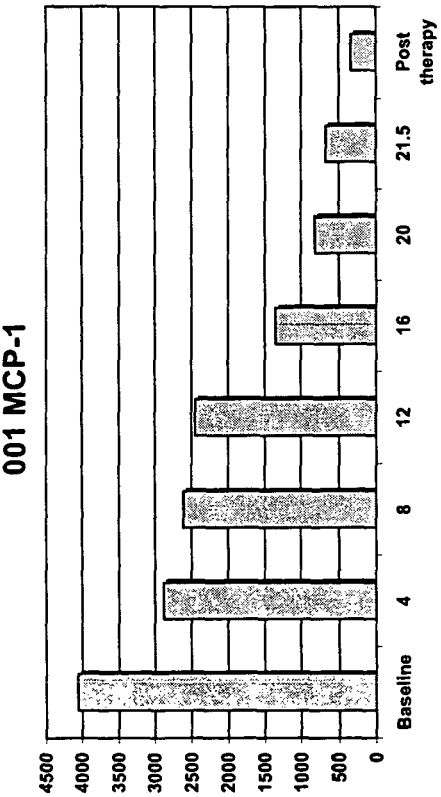
Figure 5M:
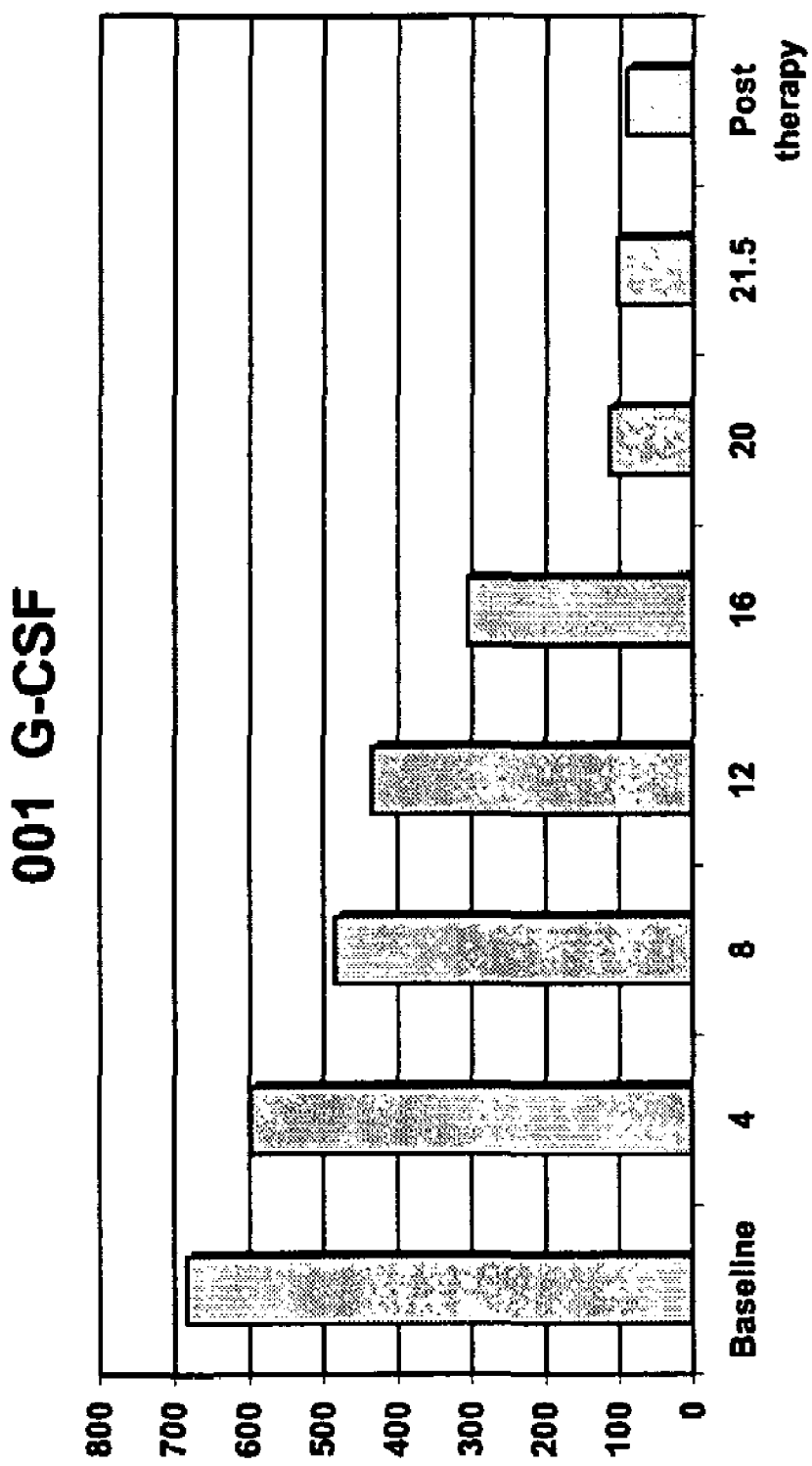

Key physiologic parameters, which contributed to the improved Apache 3 predicted mortality rates, are summarized in FIGS. 3 and 4. In FIG. 2, the systolic and diastolic blood pressures in relation to the vasopressor requirements are detailed along with key respiratory parameters. The patient's blood pressure was much more stable during RAD therapy and his pressor requirements markedly diminished during the treatment period. The increase in dopamine dosage as the RAD was placed in the circuit was required in order to maintain blood pressure during the initial phases of extracorporeal exposure to the RAD, a phenomena observed in preclinical studies and in other synthetic extracorporeal cartridges during first exposure to the patient. Within 4 to 10 hours following discontinuation of RAD therapy, the pressor requirements of the patient increased and his respiratory parameters worsened.

The effect on renal function was also striking. As seen in FIG. 3, RAD therapy had a time correlation to converting an oliguric acute renal failure state to non-oliguria. This improved urine flow was reflective of enhanced renal clearance function. The calculated creatinine clearances changed from 4.9±0.9 ml/min to 9.7±0.6 ml/min and 6.2±0.9 ml/min, 12 hours prior to, during, and 12 hours after therapy, respectively.

In addition, the 21.5 hours of treatment coincided with a reduction in plasma creatinine concentrations from 7.0 mg/dl to 6.0 mg/dl despite ongoing rhabdomyolysis as reflected with the elevated CPKs during this treatment interval. In fact, both plasma and urine myoglobin levels were greater than 100,000 ng/ml during this treatment period.

The RAD also demonstrated maintenance of excellent viability and functionality during the treatment period. Renal tubule cell counts exiting the RAD in the processed ultrafiltrate was over the treatment interval cumulatively less than 0.1% of the total renal epithelial cell number (approximately $1.0 \times 10^9$ cells) within the device. This maintained viability occurred during treatment of a critically ill uremic individual with toxic shock syndrome and marked myoglobinuria. The functionality of tubular cell function was demonstrated by the tubular fluid/ultrafiltrate glutathione (GSH) ratios, which averaged 0.72 demonstrating active breakdown and transport of amino acids by the tubule cells. Plasma 1,25-dihydroxy-vitamin $D_3$ levels also improved during the treatment interval from 15 pg/ml to 22 pg/ml (normal range=17 pg/ml to 53 pg/ml), demonstrating endocrinologic activity of the cells.

Fortunately for the patient, despite an Apache 3 score predicting as high as a 92 percent in-hospital mortality rate, he eventually improved with his liver function tests returning to normal, respiratory parameters improving with successful extubation, and a return to normal renal function, so that hemofiltration and hemodialysis was discontinued. He was discharged from the ICU after 13 days and the acute care hospital after 20 days.

The mechanism by which renal tubule cells may have affected these physiological parameters of this patient may be related to a possible role the kidney plays in immunomodulation during stress states, as suggested by preclinical large animal experiments performed by the inventor.

In this regard, plasma cytokine levels were measured in this patient prior to, during, and post-RAD therapy. Blood from the patient was collected into tubes containing sodium heparin as the anticoagulant. These tubes are immediately taken to the laboratory where they were centrifuged for 5-10 minutes at 3500 rpm to separate the blood plasma from its cellular components. The plasma was then separated into small aliquots. These aliquots were quickly frozen using liquid nitrogen before being stored at −70° C.

The cytokine assays employed a quantitative sandwich enzyme immunoassay technique. An antibody specific for the cytokine of interest was pre-coated into strips of microtiter wells by the assay kit manufacturer (R & D Systems, Inc., Minneapolis, Minn.). Technicians begin by pipetting standards with known concentrations and patient plasma samples into the wells. Any cytokine present in the plasma was bound to the wells by the immobilized antibody. After washing away unbound substances, an enzyme-linked antibody specific for the cytokine was added to the wells. Another wash was performed to remove any unbound antibody-enzyme reagent. Next, a substrate solution was added to the wells and color develops in proportion to the amount of cytokine which was bound in the initial step. The color development was then stopped and the intensity of the color was measured. Plasma cytokine concentrations were then calculated according to the color measurements of the known concentrations of the standards.

As demonstrated in Table 1 and FIG. 5, the RAD was associated with a decline in pro-inflammatory cytokine levels and an increase in anti-inflammatory cytokine levels during toxic shock, resulting in a more modulated balance.

TABLE 1

Plasma Levels of Inflammatory Proteins with RAD Therapy; Patient from Example 1.

| Protein | Normal Range | Time (hours) | | | | | | | |
|---|---|---|---|---|---|---|---|---|---|
| | | 0 | 4 | 8 | 12 | 16 | 20 | 21.5 | 25.5 |
| TNF-α (pg/ml) | <15.6 | 20 | 20 | 21 | 19 | 14 | 14 | 11 | 15 |
| STNFRI (pg/ml) | 500-2000 | 24,101 | 24,769 | 25,056 | 28,445 | 25,470 | 22,828 | — | 27,188 |
| STNFRII (pg/ml) | 950-2500 | 50,869 | 53,150 | 47,158 | — | 51,139 | 49,091 | — | 44,175 |

TABLE 1-continued

Plasma Levels of Inflammatory Proteins with RAD Therapy; Patient from Example 1.

| Protein | Normal Range | Time (hours) | | | | | | | |
|---|---|---|---|---|---|---|---|---|---|
| | | 0 | 4 | 8 | 12 | 16 | 20 | 21.5 | 25.5 |
| IL-1β (pg/ml) | <3.9 | 3 | 1 | 8 | 13 | 8 | 3 | 0 | 1.5 |
| IL-lra (pg/ml) | 50-1400 | 17,119 | 10,364 | 7,237 | 2,508 | 7,948 | 8,710 | 10,248 | 6,441 |
| IL-lsRII (ng/ml) | 2-9 | 103 | 105 | 94 | 86 | — | — | 95 | 81 |
| IFN-• (pg/ml) | <15.6 | 42 | 65 | 35 | — | 49 | 26 | — | 5 |
| IL-6 (pg/ml) | <3.13 | 833 | 736 | 853 | — | 1,255 | 784 | — | 932 |
| IL-8 (pg/ml) | <31.2 | 152 | 141 | 132 | 134 | — | — | 140 | 74 |
| MCP-1 (pg/ml) | 113-340 | 4,061 | 2,886 | 2,614 | 2,448 | 1,343 | 816 | 671 | 343 |
| MCP-1• (pg/ml) | <46.9 | <46.9 | <46.9 | <46.9 | <46.9 | — | — | <46.9 | <46.9 |
| IL-10 (pg/ml) | <7.8 | 9 | 5 | 2 | — | 2 | 5 | — | 5 |
| IL-13 (pg/ml) | <62.5 | <125 | <125 | <125 | <125 | — | — | — | <125 |
| G-CSF (pg/ml) | <39 | 684 | 598 | 485 | 435 | 307 | 114 | 104 | 90 |
| GM-CSF (pg/ml) | <7.8 | <7.8 | <7.8 | <7.8 | <7.8 | <7.8 | — | — | <7.8 |
| CRP (ng/ml) | <2000 | 650,000 | 610,000 | 865,000 | 734,000 | — | 745,000 | — | 705,000 |

Footnotes for Table 1
Hours refer to 0 = pre-therapy; 4, 8, 12, 20 of RAD therapy; 21.5 just prior to treatment discontinuation; 25.5 is 4 hours post therapy.
Blanks identify measurements not done due to sample size limitations.
Normal values are derived from derived from diagnostic kits.
Abbreviations: TNF (tumor necrosis factor)-α; STNFR (soluble TNF receptor)-I, II; IL (interleukin)-1β; IL-lra (receptor antagonist); IL-lsr (soluble receptor)-II; IFN (interferon)-•; MCP (monocyte chemoattractant protein)-1; MIP (macrophage migratory inhibitory factor)-I•; G (granulocyte)-CSF (colony stimulating factor); GM (macrophage)-CSF; CRP (C-reactive protein).

Example 2

Treatment of a Human Patient Afflicted with Acute Renal Failure with Renal Tubule Cells A 23 year old male with no significant past medical history presented to the emergency room, versed and intubated for airway protection, for work up and management of severe metabolic acidosis and unresponsiveness. He had no known drug allergies, is not on any medicines at home. He is a nonsmoker and not an illicit drug/alcohol user per family. Further, there is no history of depression or recent travel. Prior to presentation, the patient complained of abdominal pain, nausea and vomited once. The nausea and vomiting persisted for several hours. The patient was found unresponsive in a pool of vomitus.

In the emergency room, he was unconscious, afebrile, hemodynamically stable with a blood pressure (BP) of 130/80 mm of Hg and a heart rate (HR) of 90-bpm. The patient's respiratory rate was 20/min and 94% sat. Except for unresponsiveness, the examination was unremarkable with a Glasgow coma scale of 2. Initial blood work showed severe metabolic acidosis with bicarbonate of 9 mmol/l, high anion gap of 23, potassium of 7.7 mmol/l and serum creatinine of 1.1 mg/dl. ABG 7.17/19/123/7/99%. The lactic acid level was 9.3 mmol/l. CBC revealed a white blood cell (WBC) count of 12.3, hemoglobin (Hb) of 17.3 with 52.6 hematocrit (Hct) and 300 platelets. Lumbar puncture was performed and cerebral spinal fluid (CSF) showed no red blood cells (RBC), 1 WBC, 35 protein and 70 glucose. Gram stain was negative. CT head, abdomen and pelvis showed no acute process. Ammonia level was 79.

The patient was treated with intravenous fluid (IV), 6 amps of sodium bicarbonate and Ceftriaxone 2 grams IV. A gram of Phenytoin was given for twitching.

In the ICU, he was on the ventilator, with 135/70 BP and 97 bpm HR. Pupils were normal in size, reacting to light and the gag reflex was present. Reflexes were normal. The lungs were clear to auscultation bilaterally. Heart rate was regular without murmurs, rub or gallop. The abdomen was soft, nontender without hepatosplenomegaly. Bowel sounds were present. There was no peripheral edema. Occasional myoclonus was noted. No skin rash or petechie was seen.

Labs were as follows:

At 3:50 PM on the day of admission, 154 mmol/l Na, 4.8 mmol/l K, 111 mmol/l Cl, 9 mmol/l HCO$_3$, 16 mg/dl BUN, 2.2 mg/dl Cr. AG of 35. 8.7 mg/dl Ca, 6.5 mg/dl Ph, 1.9 mg/dl Mg, 6.6 g/dl T.pr, 4.1 g/dl Alb, 13 U/l AST, 82 U/l ALT, 0.4 mg/dl Bil, 12.9 PT/1.13 INR, 30.7 PTT, 17.37 WBC, 14 gms Hb, 42 HCT, 228 Plt. 11 ESR, 0.8 mg/dl CRP, 175 CPK with 5.2 MB. Osmolal gap was 5 (326-321). ABG 7.21/21/587/8/98/100% on 100% F$_i$O$_2$. 10 mmol/l lactic acid. Urine analysis showed few RBC, few WBC, 2+ protein and lots of calcium oxalate crystals. No cellular casts were seen.

Serum and urine toxicology screen was negative for acetominophen, ethanol, aspirin, tricyclic acids, opiates and cocaine. Benzodiazepines were positive in urine. Blood was sent for ethylene glycol levels. EKG showed sinus rhythm with right axis deviation and poor R wave progression. MRA of the brain did not show any bleeding or structural lesion.

IV fluids and bicarbonate replacement was continued. Ceftriaxone, Cipro and Vancomycin were given empirically after blood cultures were drawn.

At 6:00 PM on the day of admission, serum creatinine was 2.5 mg/dl with a urine output of 30 ml/hr. At 8:30 PM on the day of admission, serum creatinine was 2.8 mg/dl with decreasing urine output. Serum creatinine increased to 5 mg/dl with further decrease in the urine output by the following day. The patient was started on lasix and Diuril without adequate response. Renal ultrasound showed 11.3 cm left kidney and 11.9 cm right kidney without any hydronephrosis. CT abdomen without contrast showed enhancement of the renal cortex, consistent with toxic ingestion.

On the second day after admission, serum creatinine was 6.5 mg/dl with no urine output. ATN of unclear etiology was considered, left groin access was placed and hemodialysis was performed for eight hours with F70 kidney, 4 k bath, 300 ml/hr of ultrafiltration, 300 ml/hr BFR and 500 ml/min DFR. Ethylene glycol screen was reported as negative. However, due to the presence of mental status changes, metabolic acidosis with high anion gap and acute renal failure with crystalluria, ethylene glycol poisoning could not be ruled out.

On the third day after admission, after screening for inclusion and exclusion criteria of the Renal Tubule Assist Device (RAD) study, the patient's family was approached and consent was obtained. Labs were drawn and continuous venovenous hemofiltration (CVVH) was started at 8:45 PM in preparation to RAD therapy. Paganini risk modeling score was 130. Mental status improved and he was following commands by moving extremities.

On the fourth day after admission, the RAD was integrated into circuit at 8:53 AM and therapy was started at 9:18 AM by the RAD team. Under close monitoring of the clinical status, reabsorption of the ultrafiltrate was gradually increased to 50%. The patient tolerated the intervention well. ACT was checked every hour and glucose was checked every 15 minutes for an hour and then every hour while on RAD. Initial ACT was 172 and glucose was 214 mg/dl. DMP, CBC and ABG's were checked every four hours. Phosphorus, calcium, magnesium, albumin, uric acid and PTT/PT/INR were drawn every eight hours.

At 1:10 PM on the fourth day after admission, ACT was 186, hence heparin was decreased to 500 u/hr from 750 u/hr. A new catheter was placed and the CVVH system was changed in just 20 minutes, at 2:00 PM, due to poor blood flows through the original catheter. During this time the RAD was flushed with the replacement fluid. Subsequently, reabsorption was resumed at 50%.

After eight hours of RAD treatment (5:30 PM), the patient was reassessed and RAD was continued for another eight hours. At 9:50 PM, the hemofiltration system was changed in 3 minutes due to a clot in the venous trap.

At 1:30 AM on the fifth day after admission, the patient was again reassess and RAD was continued for another eight hours. At 1:35 AM, the hemofiltration system clotted again and was changed in 5 minutes. At this time, heparin was increased to 750 u/hr. At 7:45 AM lines were reversed due to a collapse of the catheter. At 9:00 AM, RAD therapy was discontinued, but CVVH was continued. During the course of the study, few IV fluid changes were made based on the glucose, calcium and bicarbonate values.

Figure 6:
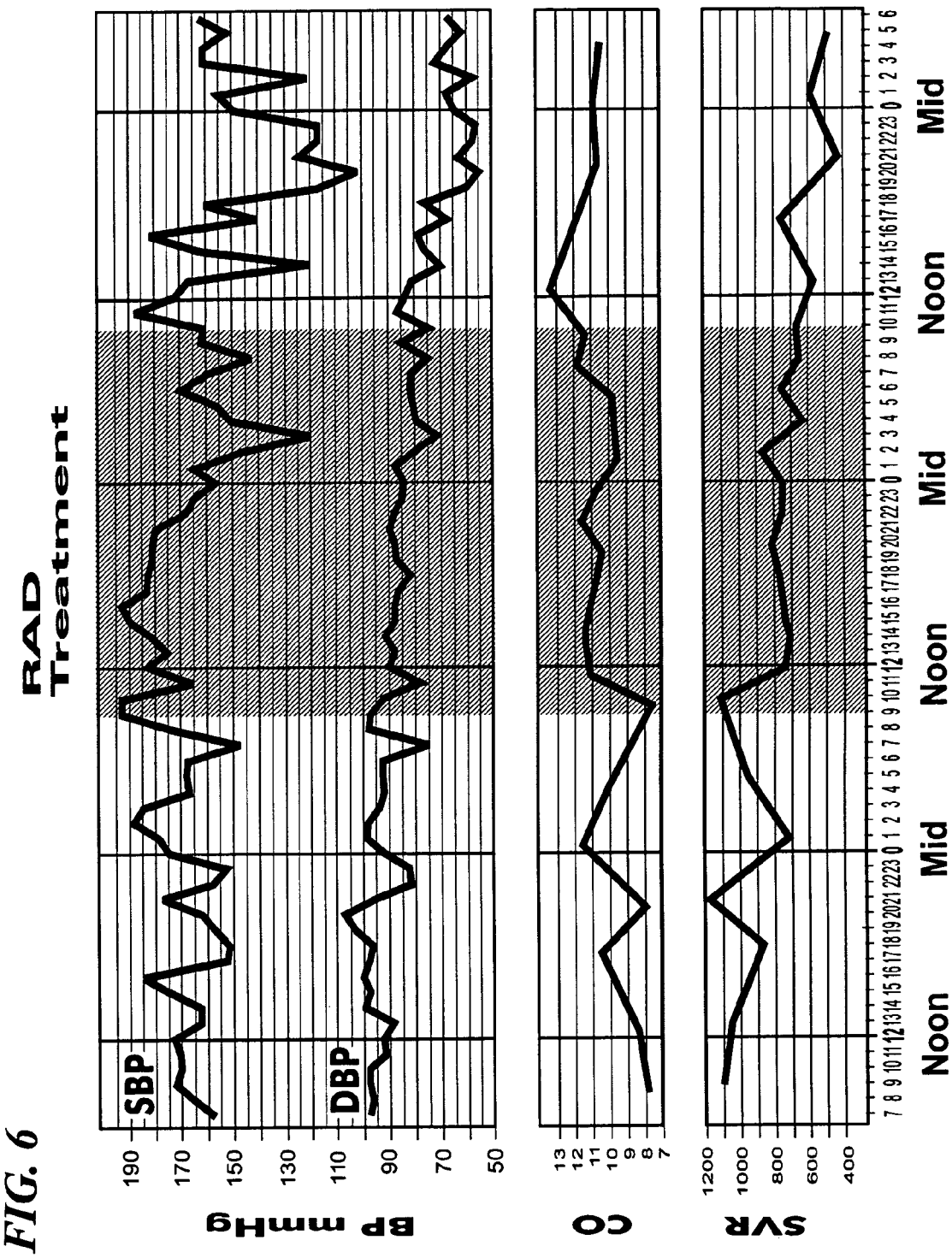
FIG. 6: Blood pressures, CO, and SVR levels in relation to time in the patient. The period of RAD treatment is represented as the shaded portion of the graph.
Figure 7:
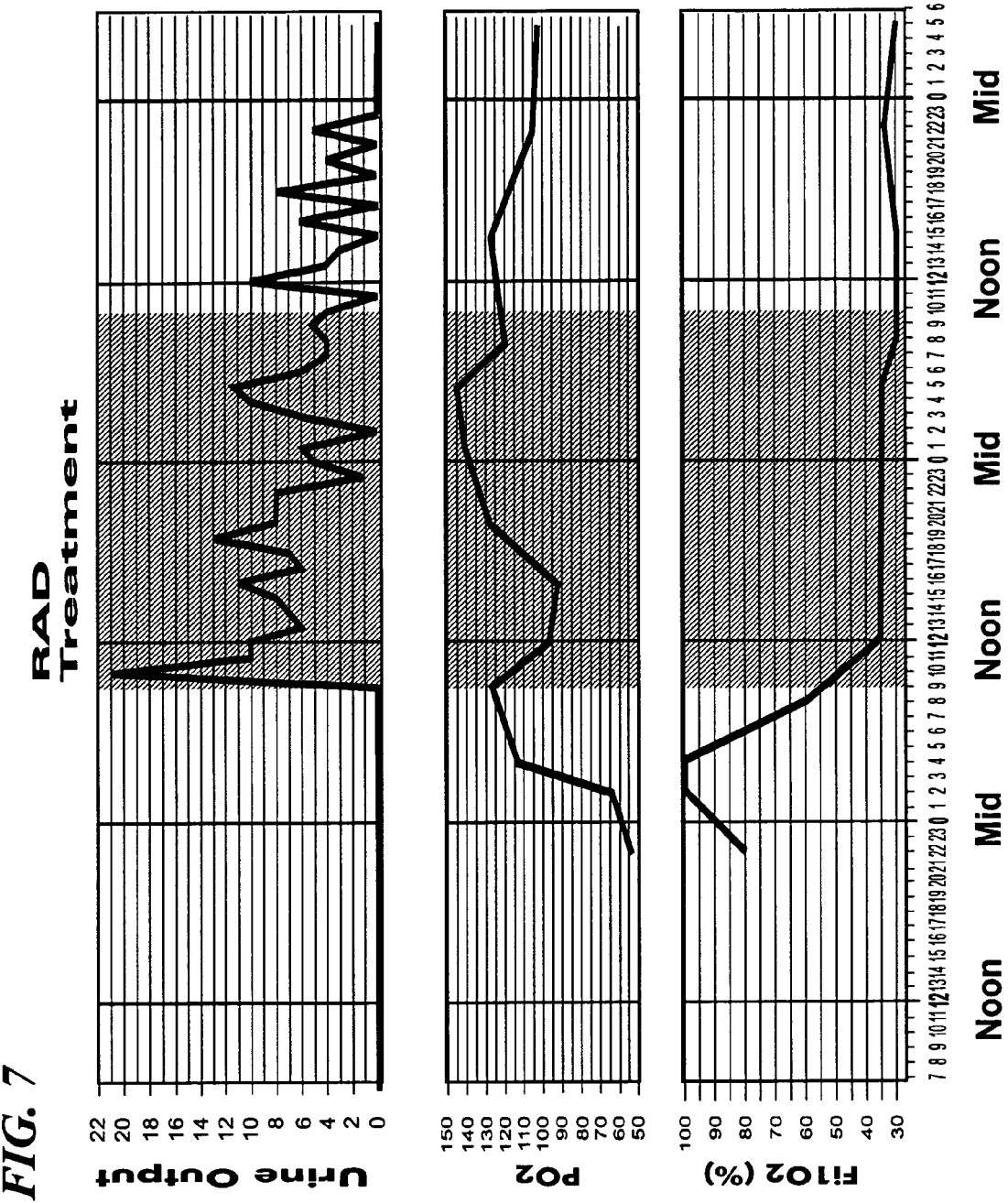
FIG. 7: Urine output and blood gases ($pO_2$ and $F_iO_2$) in relation to time in the patient. The period of RAD treatment is represented as the shaded portion of the graph.
Figure 8A:
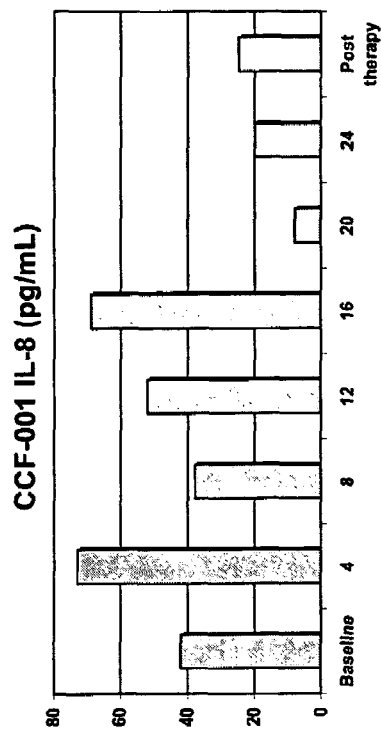
FIG. 8: Plasma cytokine levels relative to baseline pre-therapy levels. Absolute values are summarized in Table 2.
Figure 8B:
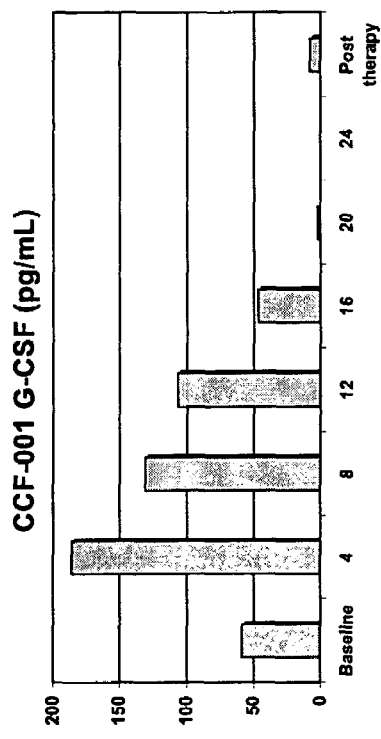
Figure 8C:
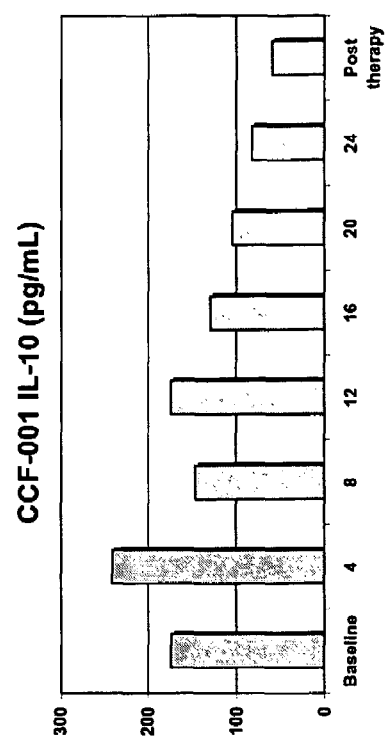
Figure 8D:
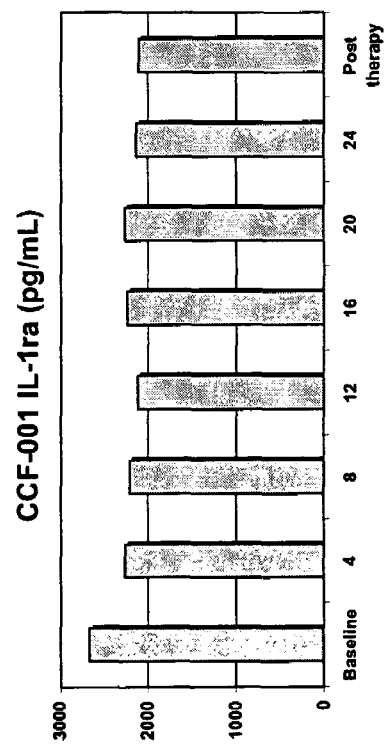
Figure 9:
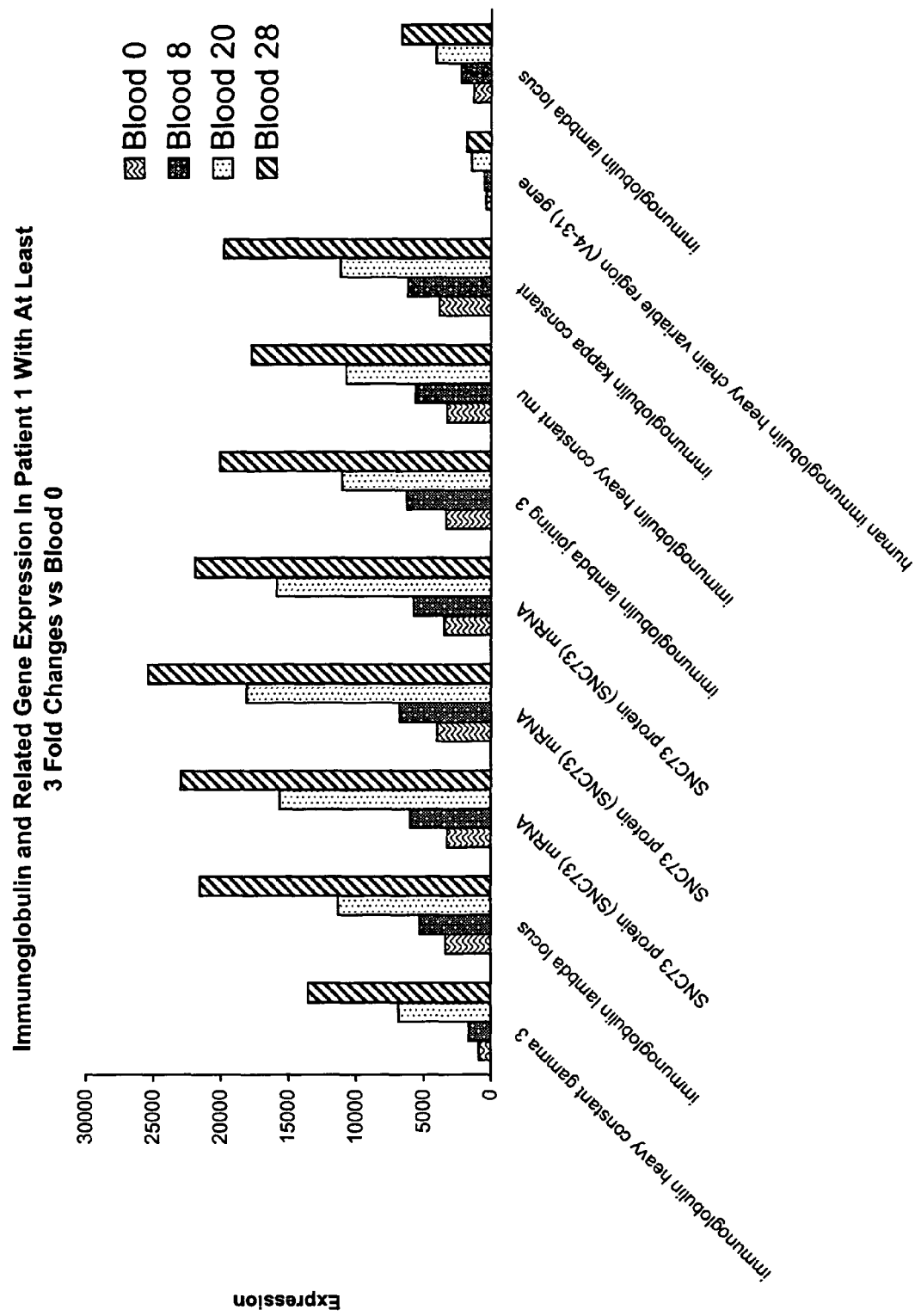
FIG. 9: Immunoglobulin and related gene expression determined by microarray analysis in patient from Example 2 with at least a 3-fold change vs. blood take pre-RAD therapy (0). 8 and 20 correspond to 8 and 20 hours of RAD therapy, respectively. And 28 represents 4 hours post 24-hour RAD treatment.
Figure 10:
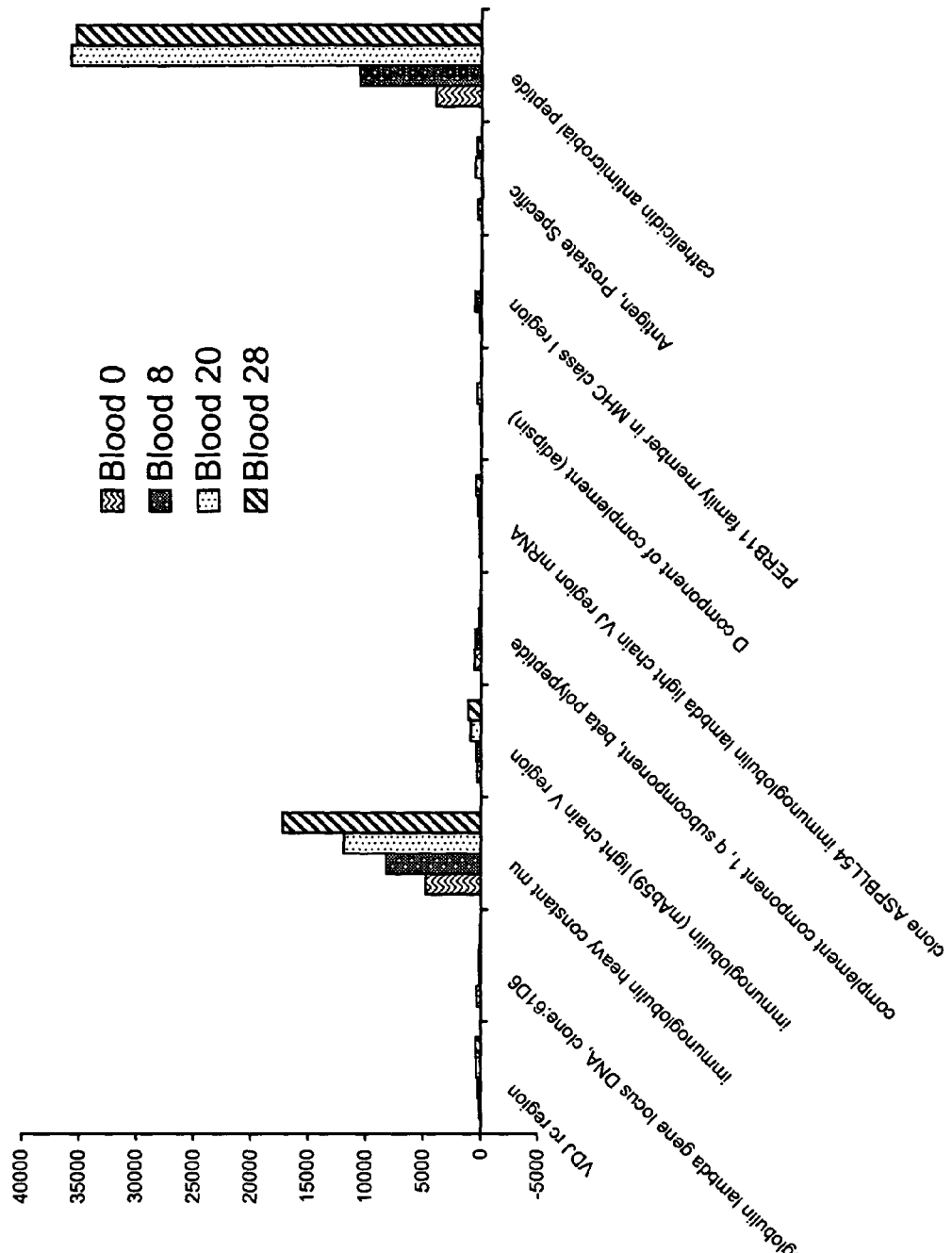
FIG. 10: Immunoglobulin and related gene expression determined by microarray analysis in patient from Example 2 with at least a 3-fold change vs. blood take pre-RAD therapy (0). 8 and 20 correspond to 8 and 20 hours of RAD therapy, respectively. And 28 represents 4 hours post 24-hour RAD treatment.
Figure 11:
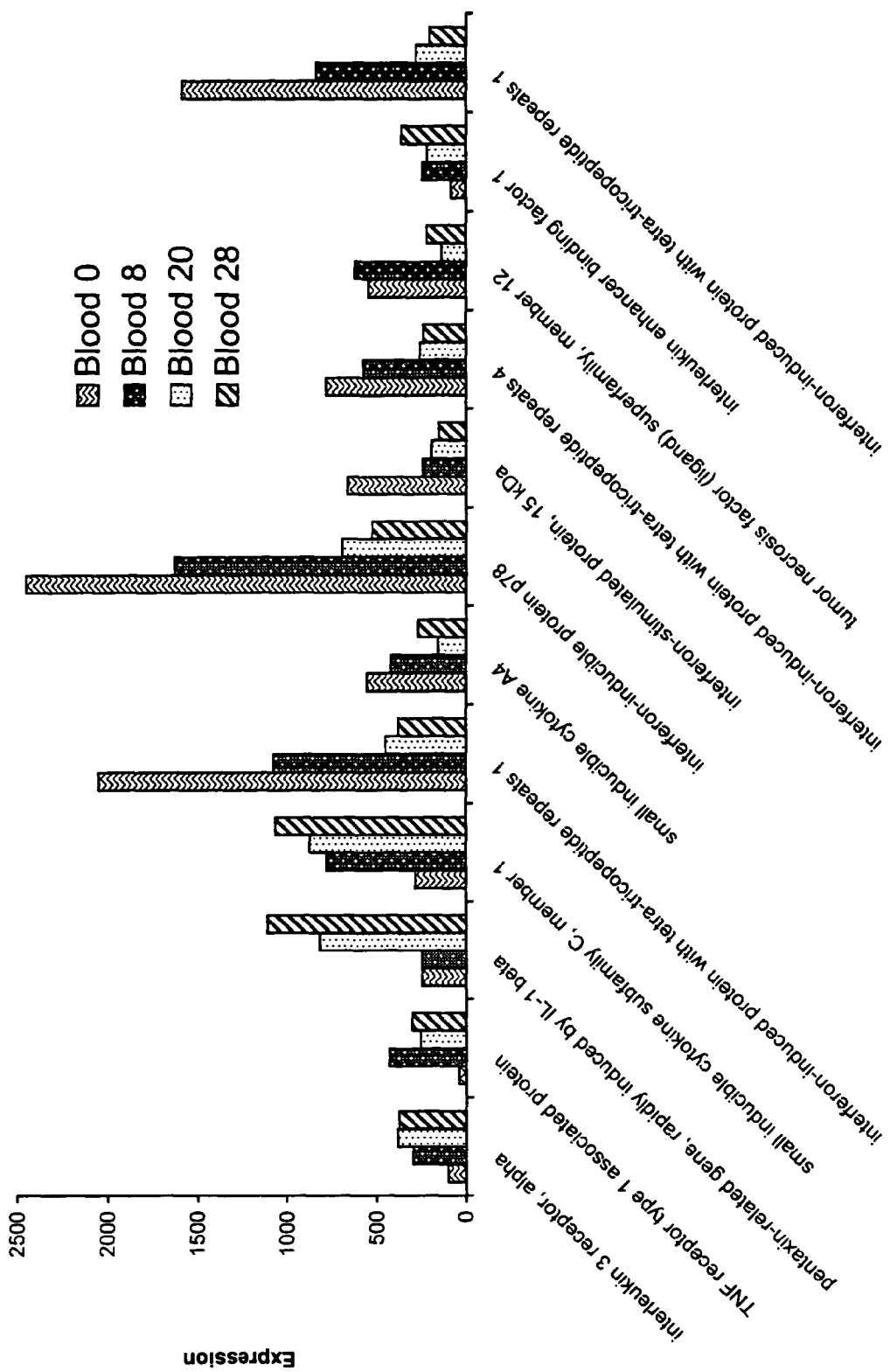
FIG. 11: Cytokine related gene expression determined by microarray analysis in patient from Example 2 with at least a 3-fold change vs. blood take pre-RAD therapy (0). 8 and 20 correspond to 8 and 20 hours of RAD therapy, respectively. And 28 represents 4 hours post 24-hour RAD treatment.
Figure 12:
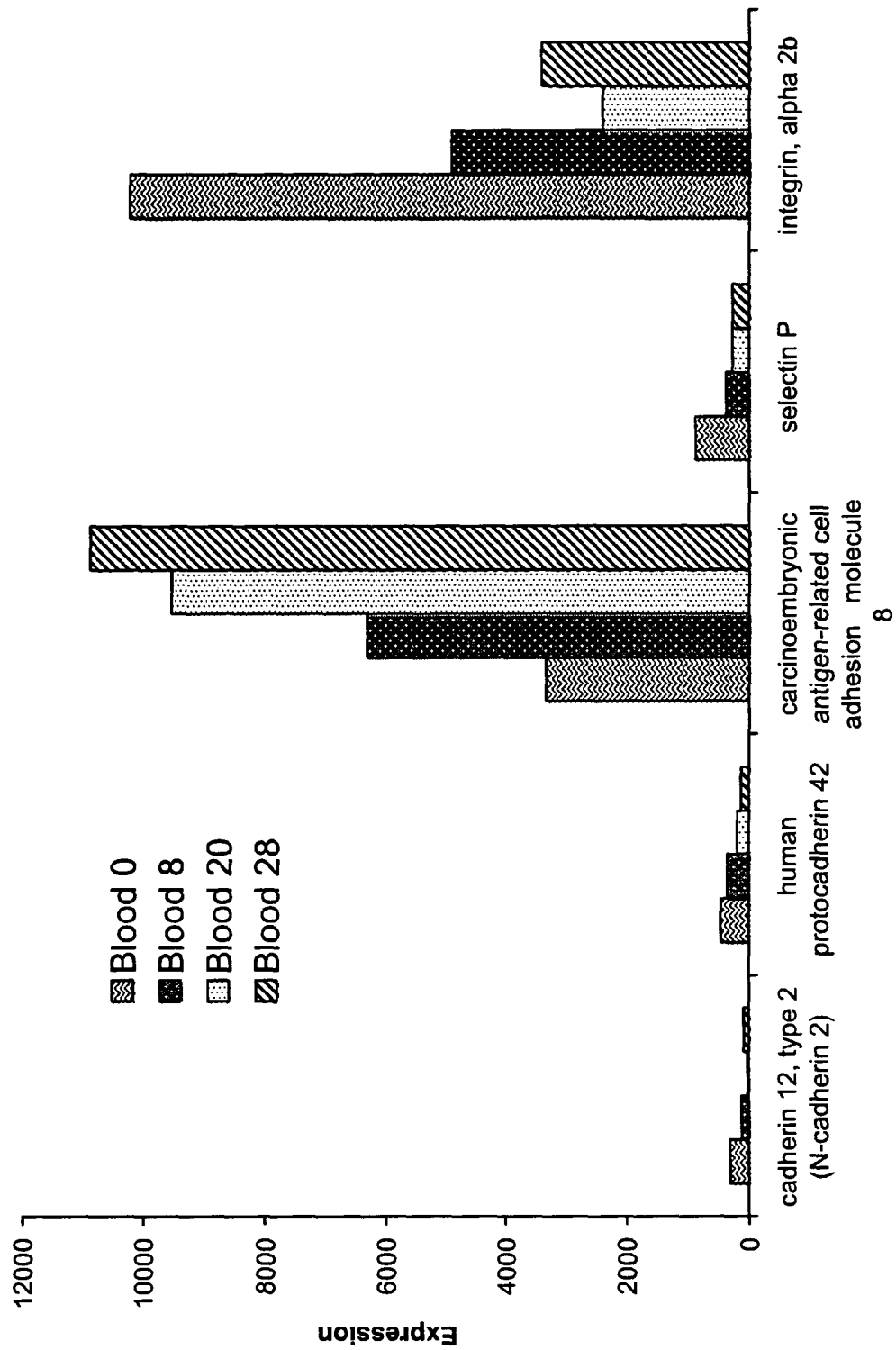
FIG. 12: Adhesion molecule expression determined by microarray analysis in patient from Example 2 with at least a 3-fold change vs. blood take pre-RAD therapy (0). 8 and 20 correspond to 8 and 20 hours of RAD therapy, respectively. And 28 represents 4 hours post 24-hour RAD treatment.

As shown in FIG. 6, hemodynamics remained stable with BP's between 170-180/80-90, during the entire study. Also in FIG. 6, SVR decreased over the course of the study from 1104 to 708-758. As the study progressed, oxygenation improved requiring lower $FiO_2$ (FIG. 7). The top panel of FIG. 7 shows that urine output increased slightly to 8-10 cc/hr while on RAD and for eleven hours post-RAD treatment. Subsequently, there was no urine output. In addition, the cardiac index improved from 4.1 to 5.8-6.0, and electrolytes and Hemoglobin/Hct remained stable.

Labs on the fifth day after admission were as follows:

142 mmol/l Na, 4.2 mmol/l K, 107 mmol/l Cl, 25 mmol/l $HCO_3$, 41 mg/dl BUN, 5.7 mg/dl Cr, 11 mg/dl CA, 2.8 mg/dl Ph, 2.6 mg/dl Mg, 721 LDH, 73 U/l AST, 65 U/l ALT, 56 U/l GGT, 0.4 mg/dl Bil, 12.8 PT/1.12 INR, 35.4 PTT, 1.1 mmol/l lactate, 12.2 WBC, 9.1 Hb, 27.1 Hct, 78 Platelet. Liver enzyme elevation and low platelets with high LDH was thought to be due to frequent system changing from clotting. A blood transfusion was given.

After discontinuation of the study, the patient continued to be anuric. CVVH was continued for solute/volume clearances. He was extubated on the eighth day after admission. Bacterial test cultures revealed no growth, therefore antibiotics were discontinued on the ninth day after admission. In addition, on the ninth day after admission, CVVH was discontinued and IHD was initiated through permcath. The urine output gradually increased to 200 cc/day by the thirteenth day after admission. At this point the patient was discharged with dialysis three times a week, accompanied by phoslo and nephrocap tablets daily.

In addition, plasma cytokine levels were measured in this patient as described in Example 1 prior to, during, and post-RAD therapy. As demonstrated in Table 2 and FIG. 8, the RAD was associated with a decline in pro-inflammatory cytokine levels (e.g., G-CSF, IL-6, IL-8, and TNF-α) and an increase anti-inflammatory cytokine levels (e.g., TNF-RI and TNF-RII) during acute renal failure.

TABLE 2

Plasma Levels of Inflammatory Proteins during RAD Therapy; Patient from Example 2.

| Protein | Normal Range | Time (hours) | | | | | | | |
|---|---|---|---|---|---|---|---|---|---|
| | | Baseline | 4 | 8 | 12 | 16 | 20 | 24 | Post Therapy |
| G-CSF (pg/ml) | <39 | 59 | 186 | 131 | 107 | 47 | 2 | 0 | 8 |
| IL-1ra (pg/ml) | 63-1397 | 2669 | 2263 | 2210 | 2119 | 2237 | 2263 | 2132 | 2106 |
| IL-1sRII (pg/ml) | 8-22 | 14360 | 15660 | — | 19908 | 20514 | — | 24675 | 20081 |
| IL-6 (pg/ml) | <12.5 | 874 | 1421 | 987 | 1242 | 915 | 726 | 581 | 158 |

TABLE 2-continued

Plasma Levels of Inflammatory Proteins during RAD Therapy; Patient from Example 2.

| Protein | Normal Range | Time (hours) | | | | | | | |
| --- | --- | --- | --- | --- | --- | --- | --- | --- | --- |
| | | Baseline | 4 | 8 | 12 | 16 | 20 | 24 | Post Therapy |
| IL-8 (pg/ml) | <31.2 | 42 | 73 | 38 | 52 | 69 | 8 | 20 | 25 |
| IL-10 (pg/ml) | <7.8 | 174 | 241 | 147 | 174 | 130 | 105 | 83 | 60 |
| IL-13 (pg/ml) | <62.5 | 60 | 74 | 49 | 46 | 46 | 43 | 63 | 51 |
| IL-18 (pg/ml) | 36.1-257.8 | 319 | 329 | 331 | 377 | 418 | 416 | 414 | 419 |
| MCP-1 (pg/ml) | 113-340 | 1506 | 1692 | 1110 | 1346 | 1808 | 1106 | 1421 | 1323 |
| MIP-1α (pg/ml) | <46.9 | 135 | 143 | 140 | 143 | 140 | 143 | 148 | 143 |
| TNF-α (pg/ml) | <15.6 | 119 | 109 | 102 | 104 | 102 | 93 | 105 | 102 |
| TNF-RI (pg/ml) | 512-1739 | 29706 | 31893 | 34035 | 37724 | 40729 | 33748 | 40905 | 36907 |
| TNF-RII (pg/ml) | 787-2145 | 26386 | 26511 | 29461 | 30689 | 32034 | 31774 | 30779 | 32258 |
| CRP (ug/ml) | <2 | 546 | 670 | 939 | 672 | 673 | 822 | 747 | 775 |
| Protein C (pg/ml) | 70-140% | 49 | 62 | 64 | 61 | 61 | 64 | 68 | 67 |

Footnotes for Table 2
Hours refer to Baseline = pre-therapy; 4, 8, 12, 20, 24 of RAD therapy, and post therapy.
Blanks identify measurements not done due to sample size limitations.
Normal values are derived from diagnostic kits.

In addition to determining the plasma cytokine levels, microarray analysis was performed to determine the levels of protein expression in the blood. Blood samples were drawn from the patient prior to initiation of RAD therapy (0 hours), after 8 hours and 20 hours of RAD therapy, and 4 hours after completion of RAD therapy (28 hours). The blood samples were treated with an anticoagulant and the blood cells were separated from plasma by centrifugation.

The white blood cells were lysed in TRIzol reagent (Gibco) and the RNA phase was separated by chloroform, total RNA was precipitated with isopropyl alcohol, and washed with 80% ethanol. Total RNA was further cleaned with RNeasy mini kit (Qiagen). First-strand cDNA was transcribed from total RNA using T7-(dT)$_{24}$ oligomer primer and SSII reverse transcriptase at 37° C. The second strand cDNA is synthesized from first-strand cDNA using DNA ligase, DNA polymerase I and T4 DNA polymerase at 16° C. (SuperScript Choice System for cDNA synthesis kit, Gibco), and then cleaned with Phase-Locking gel. Biotin-labeled cRNA is synthesized from the double strand cDNA using T7 RNA polymerase-catalyzed in vitro transcription in the presence of biotin-labeled NTP (BioArray high yield RNA transcription labeling kit, Enzo Biochem) and then fragmented at 95° C. Biotin-labeled cRNA was heated at 99° C. for 5 min in hybridization cocktail including hybridization control (Bio B, C, D, and Cre) and hybridized with at 42° C. for 16 hrs to a GeneChip® (Affymetrix), labeled with the cDNA from blood cells. The GeneChip® was then washed with non-stringent wash buffer at 50° C. and stained with streptavidin phycoerythrin (SAPE) solution. After washing at 25° C., the GeneChip® was scanned with a laser scanner (Affymetrix). The gene expression profiles were analyzed by Affymetrix Microarray Suite and Data Mining Tool software.

Figure 13:
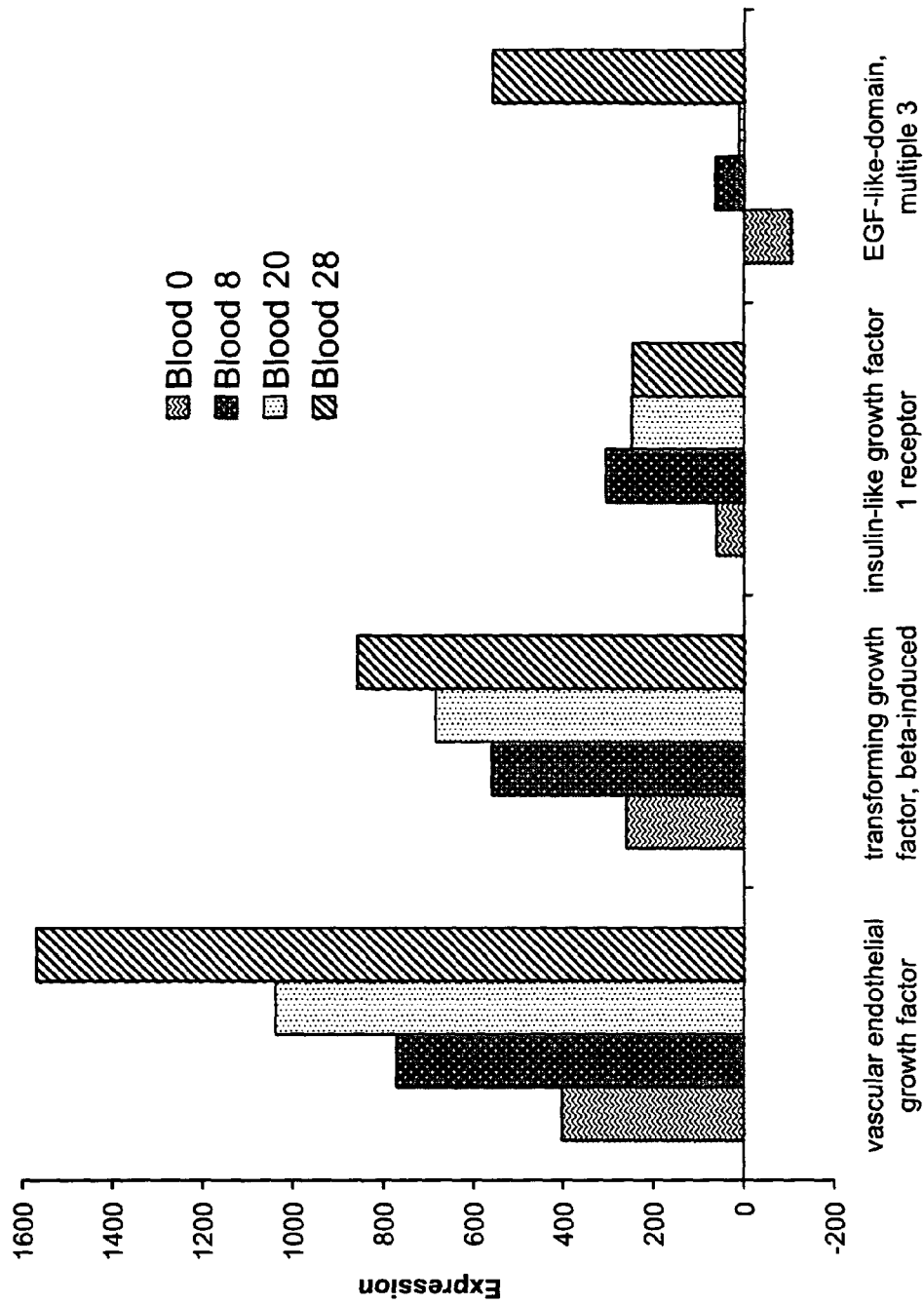
FIG. 13: Growth factor expression determined by microarray analysis in patient from Example 2 with at least a 3-fold change vs. blood take pre-RAD therapy (0). 8 and 20 correspond to 8 and 20 hours of RAD therapy, respectively. And 28 represents 4 hours post 24-hour RAD treatment.

FIGS. 9-13 shows the expression levels, as a function of time, of selected genes which are classified as immunoglobulins and related genes (FIGS. 9-10), cytokines (FIG. 11), adhesion molecules (FIG. 12), and growth factors (FIG. 13).

Example 3

Treatment of a Human Patient Afflicted with Systemic Lupus Erythematosis with Renal Tubule Cells A 26-year old woman was hospitalized in an outlying hospital. She initially presented with fever, myalgias, and arthralgias. Her work-up revealed anemia, leukopenia, thrombocytopenia, elevated liver enzymes, and a CT scan of the abdomen suggestive of cholecystitis. She underwent laporoscopic guided cholecystectomy 6 days prior to transfer. Her post-operative course deteriorated with fevers, acidosis, hyperkalemia, and anuira. Her serologies were positive for ANA and anti-dsDNA. A diagnosis of systemic lupus erythematosis (SLE) was made. After four days, high dose steroid treatment was initiated with an improvement of her pancytopenia. A repeat CT scan revealed ascites but no biliary leak. She was started on broad-spectrum antibiotics. Because of her worsening clinical status, she was transferred after 8 days to the University of Michigan Hospital.

Upon evaluation after transfer, her diagnosis of SLE and acute renal failure secondary to acute tubular necrosis was confirmed. She was also found to have severe pancreatitis with elevated serum lipase and amylase levels, rhabdomyolysis, hyperglycemia, and hypoxemia. She deteriorated rapidly and was transferred to the medical ICU the next day. She was started on CVVH and intubated secondary to acute respiratory distress syndrome (ARDS). Broad-spectrum antibiotics were continued. She subsequently developed profound hypocalcemia to 2 mg/dl requiring a calcium drop, hyperglycemia controlled with an insulin drip, lactic acidosis, elevated protime (INR=5.5), thrombocytopenia, elevated liver enzymes, and fungemia with *Candida albicans*. She was maintained on steroids and antifungal therapy begun. An emergent MRI of the abdomen confirmed the diagnosis of pancreatitis but without pancreatic necrosis.

On her fifth day in the ICU, she was enrolled into the RAD clinical trial with parent's consent. Upon initiation of RAD therapy, her blood pressure was maintained with less volume support. Within three hours of therapy, her oxygen requirements were decreased from 65% to 55% $FiO_2$. After 8 hours, $FiO_2$ was further reduced to 50% and 45% at 14 hours. She converted from a complete anuric state to an oliguric state with a urine volume of 142 ml over the subsequent 24 hours. Her Apache III predicted mortality rates were 57% for ICU and 81% for hospital stays upon initiation of therapy. During therapy the predicted mortality rates declined to 55% and 69%, respectively. The subsequent two days following a full 24 hour course of RAD treatment, the mortality rates were 56% and 63% (ICU), and 64% and 71% (hospital). By 8:00 AM the third day post-RAD therapy, the predicted mortality rate was 47% (ICU) and 57% (hospital).

The RAD performed well without adverse events during the entire 24 hour treatment interval. Early data demonstrated virtually no cell loss and active transport by the tubule cells during the course of treatment.

In addition, plasma cytokine levels were measured in this patient as described in Example 1 prior to, during, and post-RAD therapy. As demonstrated in Table 3 and FIG. 14, the RAD was associated with a modulation of pro-inflammatory cytokine and anti-inflammatory cytokine levels during treatment of systemic lupus erythematosis.

TABLE 3

Plasma Levels of Inflammatory Proteins during RAD Therapy; Patient from Example 3.

| Protein | Normal Range | Baseline | 4 | 8 | 12 | 16 | 20 | 24 | Post Therapy |
|---|---|---|---|---|---|---|---|---|---|
| G-CSF (pg/ml) | <39 | 67 | 83 | 90 | 122 | 189 | 176 | — | 10 |
| IL-1ra (pg/ml) | 63-197 | 2447 | 2945 | 1297 | 730 | 833 | 1297 | — | 146 |
| IL-1sRII (ng/ml) | 8-22 | 183 | 196 | 210 | 219 | 197 | 168 | 166 | 163 |
| IL-6 (pg/ml) | <12.5 | 38 | 83 | 100 | 213 | 404 | 312 | 172 | 94 |
| IL-8 (pg/ml) | <31.2 | 66 | 123 | 150 | 177 | 271 | 244 | 250 | 151 |
| IL-10 (pg/ml) | <7.8 | 25 | 27 | 15 | 15 | 31 | 27 | — | 35 |
| IL-13 (pg/ml) | <62.5 | 10 | 5 | 5 | 10 | 20 | 30 | — | 20 |
| IL-1β (pg/ml) | <3.9 | <14 | <14 | <14 | <14 | <14 | <14 | — | <14 |
| MCP-1 (pg/ml) | 113-340 | 869 | 2140 | 2720 | 3524 | 5899 | 4169 | — | 2243 |
| MIP-1α (pg/ml) | <46.9 | 5 | 6 | 6 | 8 | 7 | 6 | — | 11 |
| TNF-α (pg/ml) | <15.6 | 5 | 5 | 2 | 5 | 6 | 5 | — | 8 |
| TNF-RI (pg/ml) | 512-1739 | 32105 | 31722 | 33780 | 35554 | 37289 | 34465 | — | 33316 |
| TNF-RII (pg/ml) | 789-2145 | 47552 | 50987 | 53370 | 51653 | 49749 | 48078 | — | 46051 |
| IFN-γ (pg/ml) | <15.6 | <39 | <39 | <39 | <39 | <39 | <39 | — | <39 |

Footnotes for Table 3
Hours refer to Baseline = pre-therapy; 4, 8, 12, 20, 24 of RAD therapy, and post therapy.
Blanks identify measurements not done due to sample size limitations.
Normal values are derived from diagnostic kits.

Numerous modifications and variations on the present invention are possible in light of the above teachings. It is, therefore, to be understood that within the scope of the accompanying claims, the invention may be practiced otherwise than as specifically described herein.

REFERENCES

[1] Bergstrom J, Lindholm B. What are the causes and consequences of the chronic inflammatory state in chronic dialysis patients? Seminars in Dialysis 13:163-164, 2000.

[2] Bologna R, Levine D, Parker T. Interleukin-6 predicts hypoalbuminemia, hypocholesterolemia, and mortality in hemodialysis patients. American Journal of Kidney Diseases 32:107-114, 1998.

[3] Bernard G, Vincent J, Laterre P, et al. Efficacy and safety of recombinant human activated protein c for severe sepsis. NEJM 344:699-709, 2001.

[4] Kellum J. Immunomodulation in sepsis: the role of hemofiltration. Minerva Anestesiol 65:410-418, 1999.

[5] Tran D D, Groenveld A J, van der Meulen J, et al. Age, chronic disease, sepsis, organ system failure, and mortality. Critical Care Medicine 18:474-479, 1990.

[6] Donnelly S, Robertson C. Mediators, mechanisms and mortality in major trauma. Resuscitation 28:87-92, 1994.

[7] Bone R C, Fischer C J, Clemmer T P, et al. A controlled clinical trial of high-dose methylprednisolone in the treatment of severe sepsis and septic shock. NEJM 317:653-8, 1987.

[8] Horn K. Evolving strategies in the treatment of sepsis and systemic inflammatory response syndrome (SIRS). QJM 91:265-277, 1998.

[9] Breen D, Bihari D. Acute renal failure as a part of multiple organ failure: The slippery slope of critical illness. Kidney International 53 Suppl 66:S25-S33, 1998.

[10] Trznadel K, Luciak M, Paradowski M, et al. Hemodialysis and the acute-phase response in chronic uremic patients. International Journal of Artificial Organs 12:762-765, 1989.

[11] Docci D, Bilancioni R, Baldrati L, et al. Elevated acute phase reactants in hemodialysis patients. Clinical Nephrology 34:88-91, 1990.

[12] Honkanen E, Gronhagen-Riska C, Teppo A, et al. Acute-phase proteins during dialysis: Correlations with serum interleukin-1beta levels and different dialysis membranes. Nephron 57:283-287, 1991.

[13] Descamps-Latscha B, Herbelin A, Nguyen A, et al. Balance between IL-1β, TNF-α and their specific inhibitors in chronic renal failure and maintenance dialysis. Journal of Immunology 154:882-889, 1995.

[14] Herbelin A, Urena P, Nguyen A, et al. Elevated circulating levels of interleukin-6 in patients with chronic renal failure. Kidney International 39:954-960, 1991.

[15] Pereira B, Sundaram S, Snodgrass B, et al. Plasma liposaccharide binding protein and bactericidal/permeability increasing factor in CRF and HD patients. Journal of the American Society of Nephrology 7:479-487, 1996.

[16] Nockher W, Scherberich J. Monocyte cell-surface CD14 expression and soluble CD14 antigen in hemodialysis: Evidence for chronic exposure to LPS. Kidney International 48:1469-1476, 1995.

[17] Meur Y, Fixe P, Aldigier J, et al. Macrophage colony-stimulating factor involvement in uremic patients. Kidney International 50:1007-1012, 1996.

[18] Lowrie E, Lew N. Death risk in hemodialysis patients: The predictive value of commonly measured variables and an evaluation of death rate differences between facilities. American Journal of Kidney Disease 15:458-482, 1990.

[19] Lowrie E, Lew N, Huang W. Race and diabetes as death risk predictors in hemodialysis patients. Kidney International 42 Supplement 38:S22-S31, 1992.

[20] Zimmermann J, Herrlinger S, Pruy A, et al. Inflammation enhances cardiovascular risk and mortality in hemodialysis patients. Kidney International 55:648-658, 1999.

[21] Esfandiari E, McInnes I, Lindop G, et al. A proinflammatory role of IL-18 in the development of spontaneous autoimmune disease. Journal of Immunology 167:5338-5347, 2001.

[22] Perez de Lema G, Maier H, Nieto E, et al. Chemokine expression precedes inflammatory cell infiltration and chemokine receptor and cytokine expression during the initiation of murine lupus nephritis. Journal of the American Society of Nephrology 12:1369-1382, 2001.

[23] Gabay C. Cytokine inhibitors in the treatment of rheumatoid arthritis. Expert Opinion in Biological Therapy 2:135-149, 2002.

[24] Hedbom E, Hauselmann H. Molecular aspects of pathogenesis in osteoarthritis: the role of inflammation. Cell Mol Life Sci 59:45-53, 2002.

[25] Sandborn W. Strategies targeting tumor necrosis factor in Crohn's disease. Acta Gastroenterol Belg 64:170-172, 2001.

[26] Humes H, MacKay S, Funke A, et al. Tissue engineering of a bioartificial renal tubule assist device: In vitro transport and metabolic characteristics. Kidney International 55:2502-2514, 1999.

[27] Humes H, Buffington D, MacKay S, et al. Replacement of renal function in uremic animals with a tissue-engineered kidney. Nature Biotechnology 17:451-455, 1999.

[28] Humes H. Bioartificial kidney for full renal replacement therapy. Seminars in Nephrology 20:71-82, 2000.

[29] MacKay S, Funke A, Buffington, D, et al. Tissue engineering of a Bioartificial renal tubule. ASAIO Journal 44:179-183, 1998.

[30] Henderson B, Poole S, Wilson, M. Bacteria-Cytokine Interactions in Health and Disease. Portland Press Ltd, London 84-92, 1998.

[31] Kanazawa S, Tsunoda T, Onuma E. VEGF, basic-FGF, and TGF-beta in Crohn's disease and ulcerative colitis: a novel mechanism of chronic intestinal inflammation. American Journal of Gastroenterology 96:822-828, 2001.

[32] Monteleone G, MacDonald T. Manipulation of cytokines in the management of patients with inflammatory bowel disease. Annals of Medicine 32:552-560, 2000.

[33] Neurath M. Immunotherapy of inflammatory bowel diseases: current concepts and future perspectives. Archivum Immunologiae et Therapiae Experimentalis 48:81-84, 2000.

[34] Prud'homme G. Gene therapy of autoimmune diseases with vectors encoding regulatory cytokines or inflammatory cytokine inhibitors. Journal of Gene Medicine 2:222-232, 2000.

[35] Wilder R, Elenkoy I. Hormonal regulation of tumor necrosis factor-alpha, interleukin-12 and interleukin-10 production by activated macrophages. A disease-modifying mechanism in rheumatoid arthritis and systemic lupus erythematosus? Annals of the New York Academy of Sciences 876:14-31, 1999.

[36] Yarwood J, Leung D, Schlievert P. Evidence for the involvement of bacterial superantigens in psoriasis, atopic dermatitis, and Kawasaki syndrome. FEMS Microbiology Letters 192:1-7, 2000.

[37] Terui T, Ozawa M, Tagami H. Role of neutrophils in induction of acute inflammation in T-cell-mediated immune dermatosis, psoriasis: a neutrophil-associated inflammation-boosting loop. Experimental Dermatology 9:1-10, 2000.

[38] Lewis A, Manning A. New targets for anti-inflammatory drugs. Current Opinion in Chemical Biology 3:489-494, 1999.

[39] Bonifati C, Ameglio F. Cytokines in psoriasis. International Journal of Dermatology 38:241-251, 1999.

[40] Quackenbush J. Computational analysis of microarray data. Nature Rev Genet 2:418-427, 2001.

The inventioned claimed is:

1. A method of modulating the levels of at least one inflammatory cytokine in a patient in need thereof, comprising:
   contacting, outside of the kidney, at least a portion of the body fluid of the patient with renal tubule cells, wherein the patient in need thereof is suffering from one or more disease selected from the group consisting of, malnutrition, chronic congestive heart failure, inflammatory bowel disease, Crohn's disease, ulcerative colitis, rheumatoid arthritis, ankylosing spondylitis, systemic vasculitis, lupus, Wegener's granulomatosis, polyarteritis nodosa, dermatomyositis, diabetes mellitus Type I, thyroiditis, psoriasis, Guillian Barre syndrome, multiple sclerosis, and atherosclerosis, or other autoimmune disorders.

2. The method of claim 1, wherein the patient in need thereof is suffering from one or more disease selected from inflammatory bowel disease, Crohn's disease, and ulcerative colitis.

3. The method of claim 1, wherein the patient in need thereof is suffering from one or more disease selected from rheumatoid arthritis and ankylosing spondylitis.

4. The method of claim 1, wherein the patient in need thereof is suffering from one or more disease selected from systemic vasculitis, lupus, Wegener's granulomatosis, polyarteritis nodosa, and dermatomyositis.

5. The method of claim 1, wherein the patient in need thereof is suffering from one or more disease selected from Guillian Barre syndrome and multiple sclerosis.

6. The method of claim 1, wherein the patient is not afflicted with renal disease.

7. The method of claim 1, wherein the body fluid is ultrafiltrate of plasma.

* * * * *